United States Patent
Miyashita et al.

(10) Patent No.: US 6,522,908 B1
(45) Date of Patent: Feb. 18, 2003

(54) BIOMAGNETIC FIELD MEASURING APPARATUS

(75) Inventors: Tsuyoshi Miyashita, Kokubunji (JP); Keiji Tsukada, Kashiwa (JP); Akihiko Kandori, Kokubunji (JP); Shoji Kondo, Hitachinaka (JP); Hitoshi Sasabuchi, Mito (JP)

(73) Assignee: Hitachi, Ltd., Tokyo (JP)

( * ) Notice: Subject to any disclaimer, the term of this patent is extended or adjusted under 35 U.S.C. 154(b) by 302 days.

(21) Appl. No.: 09/678,654

(22) Filed: Oct. 4, 2000

(30) Foreign Application Priority Data

Oct. 6, 1999 (JP) .......................... 11-285165
Aug. 7, 2000 (JP) ........................ 2000-244013

(51) Int. Cl.$^7$ .............................................. A61B 5/05
(52) U.S. Cl. ................................................... 600/409
(58) Field of Search ................................ 600/409, 410, 600/9, 544, 545, 547; 128/897, 899, 920, 922, 923

(56) References Cited

FOREIGN PATENT DOCUMENTS

| JP | 63-311945 A | * 12/1988 | ............ A61B/10/00 |
|----|----|----|----|
| JP | 02180244 | 7/1990 | |
| JP | 3-60638 A | * 3/1991 | ............ A61B/5/05 |
| JP | 03244433 | 10/1991 | |
| JP | 3-251226 A | * 11/1991 | ............ A61B/5/05 |
| JP | 3-272738 A | * 12/1991 | ............ A61B/5/05 |
| JP | 04109929 | 4/1992 | |
| JP | 04303416 | 10/1992 | |
| JP | 8-238225 A | * 9/1996 | ............ A61B/5/05 |
| JP | 10305019 | 11/1998 | |

OTHER PUBLICATIONS

Recent Advances In Biomagnetism Proceedings of the 11$^{th}$ International Conference on Biomagnetism Published by Tohoku University Press, Sendai, 1999 pp. 177–180.

* cited by examiner

Primary Examiner—Hieu T. Vo
(74) Attorney, Agent, or Firm—Antonelli, Terry, Stout, & Kraus, LLP

(57) ABSTRACT

First and second markers are disposed respectively on the processus xiphoideus and the incisura jugularis of the subject to be inspected. The chest of the subject is positioned below the cryostat so that a line joining the first and second markers extends in one direction in which sensors are arranged in the interior of the cryostat. Processing includes (1) forming, from magnetic waveform signals, an image representing the activity of the heart of the subject, (2) making the pixel size of a morphological image, including the heart photographed by an image pickup device, coincident with the pixel size of functional information and forming a functional image equal in pixel size to the morphological image, (3) making the position of the first marker in the functional image and the position of the first marker in the morphological image coincident, and (4) combining the functional image and the morphological image.

19 Claims, 12 Drawing Sheets

BIOMAGNETIC FIELD MEASURING APPARATUS

BACKGROUND OF THE INVENTION

The present invention relates to a biomagnetic field measuring apparatus using SQUID (Superconducting Quantum Interference Device) sensors, which are superconducting devices for detecting a very weak magnetic field generated from a living body. Particularly, the invention is concerned with a biomagnetic field measuring apparatus and method capable of easily obtaining a combined image of functional information on the activity of the heart of a subject to be inspected and a morphological image of the heart, as well as a data processing method and a positioning method for the subject to be inspected using the biomagnetic field measuring apparatus.

In a conventional biomagnetic field measuring apparatus for measuring the function of the brain, as shown in FIG. 16, plural detecting coils 12 are arranged on a bottom 11 of Dewar whose external form is in conformity with the curvature of the head, magnetic field generating coils 13, which are mounted at plural positions of the head, are energized and the resulting magnetic field is detected by the detecting coils 12. Further, a relation between the magnetic field generated by the magnetic field generating coils 13 and the output of the detecting coils 12 is simulated. The positions of the magnetic field generating coils 13, which minimize the difference between the measured data detected by the detecting coils 12 and the output of the detecting coils 12 after the simulation, are estimated to specify position coordinates at the head positions where the magnetic field generating coils 13 are arranged (see, for example, JP-A-No. Hei 4-303416).

As shown in FIG. 17, in measuring a morphological image of a head by an MRI (magnetic resonance imaging) device, MRI markers 21 are arranged at the same positions as the head positions where the magnetic generating coils 13 shown in FIG. 16 are arranged, and a tomogram of the entire head, including the MRI markers 21, is measured. Then, position coordinates of the MRI markers 21 are specified using an MRI image (see, for example, JP-A-No. Hei 4-303416).

In combining the results of measurement of the brain magnetic field with the MRI image of the head, which represents a form, there is determined a relation between the position coordinates of the magnetic field generating coils 13 and the position coordinates of the MRI markers 21. For example, when the position of an active brain site obtained by measuring the brain magnetic field is to be displayed on the morphological image, a tomogram of the brain is reconstructed so as to include coordinates corresponding to the position of the active site with use of the head tomogram obtained by the MRI device, and then the active site of the brain and the MRI image are combined and displayed (see, for example, A. Uchida et al., AVS[th] based Brain Activity Analysis System with a Real Head Shape, Recent Advances in Biomagnetism, Edited by Y. Yoshimoto et al., Tohoku University Press, pp.177–180, 1999).

In connection with a biomagnetic field measuring apparatus, various methods have been reported for establishing a positional relation between a subject to be inspected on a bed and a Dewar (see, for example, JP-A-Nos. Hei 3-244433, Hei 2-180244. and Hei 4-109929).

SUMMARY OF THE INVENTION

In case of applying the above conventional technique in the measurement of a brain magnetic field to the measurement of a biomagnetic field generated from the chest of a living body, the conventional technique involves a problem in that a complicated simulation calculation is needed for specifying position coordinates of the magnetic field generating coils arranged to specify position coordinates of a head in the measurement of a brain magnetic field and a problem in that, in the case of an MRI image, it is necessary to read MRI markers.

Moreover, in combining the results of having measured a brain magnetic field with an MRI image, it is necessary to determine a relation between coordinates of the magnetic field generating coils and coordinates of MRI markers, and it is also necessary to perform a calculation for reconstructing a tomogram of the head so as to include coordinates corresponding to the position of an active site of the brain with use of a tomogram obtained by an MRI device.

It is an object of the present invention to provide a biomagnetic field measuring apparatus which is capable of solving the above-mentioned problems of the prior art. Particularly, the present invention aims at providing a biomagnetic field measuring apparatus and a method capable of realizing, in a short time and easily, an operation for aligning the position of the heart of a subject to be inspected with a sensor array and an operation for obtaining a large signal output from SQUID (Superconducting Quantum Interference Device) sensors.

It is another object of the present invention to provide a biomagnetic field measuring apparatus which is capable of easily forming and displaying a combined image of functional information on the activity of the heart obtained from the biomagnetic field measuring apparatus with a morphological image obtained by an image pick-up device other than the biomagnetic field measuring apparatus.

It is a further object of the present invention to provide a data processing method for displaying a combined image in the biomagnetic field measuring apparatus, as well as a positioning method which is suitable for establishing a position of a subject to be inspected using the biomagnetic field measuring apparatus at the time of displaying the combined image.

The following description is directed to typical constructions of biomagnetic field measuring apparatuses according to the present invention.

A biomagnetic field measuring apparatus according to the present invention is provided with a bed for supporting a subject to be inspected thereon, a bed support, a cryostat for cooling a plurality of SQUID sensors, and a gantry fixed to a floor surface for holding the cryostat at a known distance with respect to the floor surface. The bottom of the cryostat and an upper surface of the bed are positioned substantially in parallel with the floor surface.

The cryostat is provided at an outer peripheral surface of its bottom with an xz marking which represents an xz plane of a coordinate system (x, y, z) and a yz marking which represents a yz plane of the coordinate system. In the coordinate system (x, y, z), the xy plane is parallel to the bottom of the cryostat and z axis is perpendicular to the bottom of the cryostat.

A plurality of SQUID sensors are arranged, respectively, in x and y directions near an inner bottom of the cryostat to detect a component in the z direction of a magnetic field which is generated, for example, from the heart of the subject to be inspected. As such plural SQUID sensors, fluxmeters which detect components in both x and y directions of a magnetic field generated from the heart of the subject to be inspected may be used.

An optical system is used to adjust a positional relation between the bottom of the cryostat and the bed. The optical system comprises a first laser source for generating a first sectorial laser beam which spreads sectorially in the xz plane, a second laser source for generating a second sectorial laser beam which spreads sectorially in yz plane, and a third laser source for generating a dot-like laser beam which is radiated to the bed surface obliquely across the first and second sectorial laser beams. The first laser source is fixed to a frame which is secured to the gantry; the second laser source is fixed to a frame which is secured to the bed support; and the third laser source is fixed to a frame which is secured to any of the floor surface, ceiling, and wall surface.

As means for changing irradiating directions of the laser beams generated respectively from the three laser sources, there are first position changing means which changes the irradiating direction of the first sectorial laser beam so as to irradiate the xz marking, second position changing means which changes the irradiating direction of the second sectorial laser beam so as to irradiate the yz marking, and third position changing means which changes the irradiating direction of the dot-like laser beam so as to irradiate a crossing line between the first and second sectorial laser beams and also irradiate a crossing point between the z axis and the bed surface.

As means for moving the bed position with respect to the bottom of the cryostat, there are x direction moving means which moves the bed support in x direction on the floor surface, y direction moving means which moves the bed in y direction on the bed support, and z direction moving means which moves the bed in z direction on the bed support.

With movement of the bed position relative to the cryostat bottom, the distance between the bed and the floor surface is measured automatically by distance measuring means and the measured value is displayed on a display unit.

According to this construction, the first and second sectorial laser beams from the first and second laser sources, respectively, and the dot-like laser beam from the third laser source have their irradiating directions changed and the bed is moved in x, y, and z directions. With a simple construction, a vertical position of the bed can be measured and it is possible to adjust the positional relation between the subject to be inspected on the bed and the cryostat bottom.

In another typical construction of a biomagnetic field measuring apparatus according to the present invention, a plurality of SQUID sensors for detecting a normal line component of a magnetic field generated from the heart of a subject to be inspected are arranged in two dimensions on an inner bottom of a cryostat (Dewar) and are cooled to a low temperature. The SQUID sensors are driven by a drive circuit and magnetic waveform signals of the normal line component detected by the SQUID sensors are collected by means of a processing unit, such as a computer, which performs an arithmetic processing and controls various portions of the apparatus. Prior to the measurement, a first marker indicative of a first reference point is disposed on the body surface at a first point of the chest of the subject to be inspected and a second marker indicative of a second reference point is disposed on the body surface at a second point of the chest.

A coordinate system (x, y, z) is established in the biomagnetic field measuring apparatus and a positional relation between the chest surface of the subject to be inspected on the bed and a bottom surface of the Dewar is adjusted using a total of three laser beams, which include a sectorial laser beam spreading sectorially in the xz plane, a sectorial laser beam spreading sectorially in a plane parallel to the yz plane, and a dot-like laser beam which is radiated to the bed surface obliquely across those two sectorial laser beams. The xy plane of the coordinate system (x, y, z) is set on a measuring plane for measurement with the SQUID sensors. The bottom of Dewar is parallel to all of the xy plane, measuring plane and bed upper surface, and the distance between the bed upper surface and the Dewar bottom is known.

The bed is moved in the z direction up to a position sufficiently higher than the height of the body surface of the subject to be inspected, which height has been measured with the bed adjusted to its lowest height. Then using the three laser beams, the irradiating direction of the dot-like laser beam is set so as to irradiate a crossing point between the z axis and the bed surface, and the distance between the Dewar bottom and the bed upper surface is measured. The bed is brought down to a low position, and the subject to be inspected is laid on the bed. Then the sectorial laser spread in the yz plane is moved in the x direction so as to pass through the first and second reference points, and the position of the subject to be inspected is adjusted so that the line joining the first and second reference points becomes parallel or coincident with one direction in which the centers of the SQUID sensors are arranged.

Next, the bed is moved in the y direction so that the sectorial laser spread in the xz plane passes through the first reference point. Further, the bed is moved in the x direction so that the sectorial laser beam spread in a plane parallel to the yz plane becomes coincident with the yz plane, and, thereafter, the bed is moved in the z direction until the irradiation point of the dot-like laser beam becomes coincident with the first reference point. Then, the bed is moved in the z direction until the body surface of the subject to be inspected comes into contact with the bottom of the Dewar and the amount of the movement is detected.

Since an initial distance between the bottom of the Dewar and the first reference point and the amount of the movement of the bed are known, it is possible to determine the distance between the Dewar bottom and the first reference point when the body surface contacts the bottom of the Dewar. Since the positions of processus xiphoideus and incisura jugularis can be determined by touch easily with a high reproducibility, it is preferable to select, as the first point, a body surface position of processus xiphoideus of the subject to be inspected and, as the second point, to select a body surface position of incisura jugularis of the subject to be inspected.

The processing unit executes a data processing method comprising (1) a processing of forming, from a magnetic waveform signal, an image which represents functional information relating to the activity of the heart of the subject to be inspected; (2) a processing in which the pixel size of the image representing the functional information is made coincident with the pixel size of a morphological image of the chest of the subject to be inspected, and there is formed a functional image having the same pixel size as that of the morphological image in which a first marker indicating the first reference point is disposed on the body surface at the first point of the chest of the subject to be inspected; (3) a processing of bringing the position of the first reference point in the functional image into coincidence with the position of the first marker in the morphological image; and, (4) a processing of forming a combined image of the functional image and the morphological image. Prior to the processing (4) there is performed a processing (3') of rotating the morphological image around the first reference point and thereby making the pixel arrangement direction in the body axis direction of the subject to be inspected in the morphological image and that in the functional image coincident with each other.

Further, in connection with the processing (1), the processing unit executes the following data processing method comprising steps (a) to (e). (a) There are performed a processing of estimating an activated position of the heart of the subject to be inspected as a current source, using a magnetic waveform signal of a magnetic field component in a normal line direction which has been measured, and a processing of forming an image including the position of the current source as an image which represents functional information. Further, a processing is carried out to obtain a tangential magnetic field component of a magnetic field generated from the heart of the subject to be inspected, and the following processings are conducted using a magnetic waveform signal of the tangential magnetic field component. (b) There is performed a processing of forming an isomagnetic field map wherein coordinate points equal in magnetic field intensity are connected together and which is obtained as an image representing functional information. (c) There is performed a processing of forming an arrow map which represents an activated position of the heart of the subject to be inspected as a two-dimensional current distribution and which is obtained as an image representing functional information. (d) There is performed a processing of integrating a magnetic waveform in a temporal interval which contains a specific period of the heart activity of the subject to be inspected, to determine an integral intensity, and forming an isointegral map wherein coordinate points equal in integral intensity are connected together and which is obtained as an image representing functional information. (e) There is performed a processing of integrating magnetic waveforms of tangential magnetic field components in a temporal interval including two different periods of the heart activity of the subject to be inspected, to determine integral intensities, and forming an isointegral map wherein coordinate points equal in the value of difference between integral intensities in the temporal period including two different periods are connected together and which is obtained as an image representing functional information.

The morphological image is selected, for example, from any of a tomogram nearly parallel or perpendicular to the chest surface of the subject to be inspected, which has been photographed by an MRI device, a tomogram nearly parallel or perpendicular to the chest surface of the subject to be inspected, which has been photographed by a three-dimensional XCT (X-ray computed tomography) device, and an X-ray image of the subject to be inspected, which has been photographed by an X-ray camera. Using the thus-selected image and any of the images representing functional information which have been obtained in the above processings (a) to (e), the processing unit executes the data processing method including the foregoing processings (2) to (4) and (3').

According to the constitution of the present invention described above, prior to detecting a magnetic field generated from the heart of the subject to be inspected, the positional relation between the chest surface of the subject to be inspected on the bed and the bottom surface of the Dewar can be adjusted with a simple construction using a total of three laser beams, which include two sectorial laser beams and one dot-like laser beam.

As a result, substantially the whole of projection of the heart on the sensor array surface is positioned within the region of the sensor array, and the body surface of the chest of the subject to be inspected comes into contact with the lower surface of the Dewar, whereby there is obtained a large signal output. The above positional relation adjusting operation can be done in a short time and easily.

According to the present invention, moreover, such complicated calculations as simulation calculation relating to the generation of a magnetic field for estimating a magnetic field source and a reconstructing calculation for a tomogram are not performed, and a combined image can be formed and displayed easily from biofunctional information and a morphological image (tomogram) or a transmitted image, such as an X-ray image of the chest obtained by an X-ray camera. The biofunctional information is obtained by the biomagnetic field measuring apparatus, and is especially functional information on the activity of the heart, which is represented in terms of an isomagnetic field map, an arrow map, or an isointegral map, obtained from a magnetic waveform resulting from measuring a magnetic field generated from the heart, or the result of having estimated the position of a current dipole, the morphological image being obtained by a magnetic resonance imaging (MRI) device or a three-dimensional X-ray computed tomography (XCT) device and being substantially parallel or perpendicular to the chest surface.

In the MRI device or the three-dimensional XCT device, in many cases, the bed for supporting the subject to be inspected thereon is held horizontally, and, in image photographing, the subject to be inspected is laid on the bed so that the long axis direction of the bed and the body axis of the subject to be inspected are almost coincident with each other. In obtaining a chest X-ray image (X-ray transmitted image) using an X-ray camera, the subject to be inspected is in many cases photographed in a standing state or in an upright sitting state on a chair or is sometimes photographed while lying on a bed in a general hospital building.

Even when the long axis direction of the bed and the body axis of the subject to be inspected are not in exact agreement with each other during photographing in the MRI device or three-dimensional XCT device, the body axis direction of the subject to be inspected in the morphological image and the pixel arrangement direction in the body axis direction of the subject to be inspected (the direction joining the first and second reference points) in the functional image can be made coincident with each other by performing the foregoing processing (3').

More particularly, since it is possible to prepare a combined image of the functional image and an image obtained by rotating the morphological image around the first reference point (a central position of an MRI marker image or of an X-ray marker image), it is possible to obtain a more accurate combined image of both the functional image and the morphological image. For example, such an accurate combined image can be obtained by rotating the morphological image around the first reference point (a central position of an X-ray marker image) so that a center line of the backbone in a chest X-ray image (X-ray transmitted image) and the pixel arrangement direction in the body axis direction of the subject to be inspected in the functional image become coincident with each other.

A typical construction of the biomagnetic field measuring apparatus for obtaining a combined image of an image which represents biofunctional information with a morphological image will now be outlined with reference to FIG. 2. A marker 37 which represents a first reference point is disposed on the surface of processus xiphoideus of a subject 35 to be inspected, and a second marker 38 which represents a second reference point is disposed on the surface of incisura jugularis. The chest of the subject to be inspected is disposed below the bottom of a cryostat 36 in such a manner that a line joining the first and second reference points extends along one direction of the arrangement of SQUID sensors in the interior of the cryostat.

A processing unit executes (1) a processing of forming, from a magnetic waveform signal, an image which represents functional information relating to the activity of the heart of a subject to be inspected; (2) a processing of making the pixel size of a morphological image, including the heart photographed by an image pickup device, coincident with the pixel size of an image which represents functional information to form a functional image having the same pixel size as that of the morphological image, with a first-marker indicative of a first reference point being disposed on the surface of processus xiphoideus; (3) a processing of making the position of the first reference point in the functional image and that in the morphological image coincident with each other; and (4) preparing a combined image of both the functional image and the morphological image. In this way the combined image can be obtained easily without requiring any complicated calculation.

According to this construction, particularly in detecting a magnetic field generated from the heart of the subject to be inspected, substantially the whole of the projection of the heart on the sensor array surface is positioned within the region of the sensor array, and the chest surface of the subject to be inspected comes into contact with a lower surface of the Dewar, whereby the operation for affording a large signal output can be effected in a short time and easily.

According to this construction, moreover, without performing such complicated calculations as a simulation calculation relating to the generation of a magnetic field and a tomogram reconstructing calculation, it is possible to easily form and display a combined image of functional information and a morphological image (tomogram) or a transmitted image, such as a chest X-ray image obtained by an X-ray camera, the functional information relating to the activity of the heart and being represented in terms of an isomagnetic field map, an arrow map, or an isointegral map, obtained from a magnetic waveform resulting from measuring a magnetic field generated from the heart, or the result of having estimated the position of a current dipole, the morphological image being obtained by an MRI device or a three-dimensional XCT device and being substantially parallel to the chest surface.

BRIEF DESCRIPTION OF THE DRAWINGS

Other objects and advantages of the invention will become apparent from the following discussion when taken with reference to the accompanying drawings, wherein.

DESCRIPTION OF THE PREFERRED EMBODIMENTS

Figure 1:
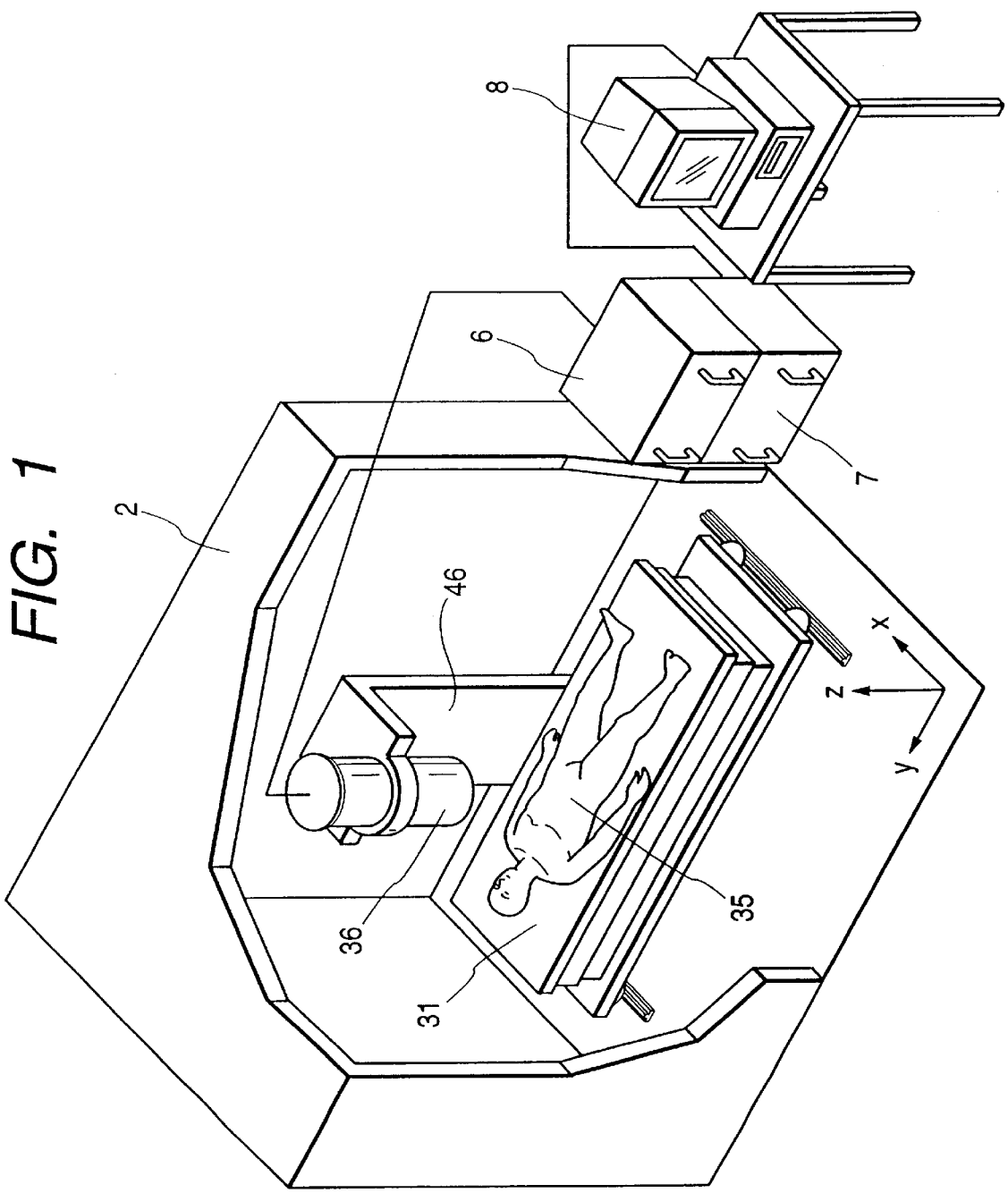
FIG. 1 is a perspective view which shows a construction of the whole of a biomagnetic field measuring apparatus according to the first embodiment of the present invention.

The biomagnetic field measuring apparatus of the present invention is provided with a bed, a bed support, a cryostat, and a gantry. Near an inner bottom of the cryostat there are disposed plural SQUID sensors in x and y directions, and they are cooled. An xz marking and a yz marking representing the xz plane and the yz plane, respectively, of a coordinate system (x, y, z) are affixed to an outer peripheral surface of the bottom of the cryostat in the coordinate system (x, y, z), the xy plane is parallel to the bottom of the cryostat, and the z axis is perpendicular to the bottom of the cryostat.

The gantry, which holds the cryostat, is fixed to a floor surface. The distance between the cryostat bottom and the floor surface is a preset known distance value, and the cryostat bottom is in a fixed position with respect to the floor surface. The cryostat bottom and the upper surface of the bed are substantially parallel to the floor surface.

As the plural SQUID sensors, there are fluxmeters for detecting a magnetic field component in the z direction or fluxmeters for detecting magnetic field components in the x and y directions.

As an optical system for use in adjusting the positional relation between the cryostat bottom and the bed there is an optical system comprising a first laser source for generating a first sectorial laser beam, which spreads sectorially in the xz plane, a second laser source for generating a second sectorial laser beam which spreads sectorially in the yz plane, and a third laser source for generating a dot-like laser beam obliquely toward the surface of the bed so as to intersect the first and second laser beams. The first laser source is fixed to a frame which is secured to the gantry; the second laser source is fixed to a frame which is secured to the bed support; and the third laser source is fixed to a frame which is secured to any of the floor surface, ceiling, and wall surface.

As means for changing the irradiating directions of the laser beams generated from the three laser beam sources there are first position changing means for changing the irradiating direction of the first sectorial laser beam so as to irradiate the xz marking, second position changing means for changing the irradiating direction of the second sectorial laser beam, so as to irradiate the yz marking, and third position changing means for changing the irradiating direction of the dot-like laser beam, so as to irradiate a crossing line between the first and second sectorial laser beams and also irradiate a crossing point between the z axis and the bed surface.

As means for moving the bed position with respect to the bottom of the cryostat, there are x direction moving means for moving the bed support in the x direction on the floor surface, y direction moving means for moving the bed in the y direction on the bed support, and z direction moving means for moving the bed in the z direction on the bed support.

As the bed position shifts relative to the bottom of the cryostat, the distance between the bed and the floor surface is measured automatically by distance measuring means, and the measured distance is displayed on a display unit.

To the biomagnetic field measuring apparatus described above, there are applied the following typical positioning method and biomagnetic field measuring method.

A typical subject-to-be-inspected positioning method for the biomagnetic field measuring apparatus according to the present invention comprises (1) setting an irradiating direction of the first sectorial laser beam so as to irradiate the xz marking; (2) setting an irradiating direction of the second sectorial laser beam so as to irradiate the yz marking, (3) setting an irradiating direction of the dot-like laser beam so as to irradiate a crossing line between the first and second laser beams and also irradiate a crossing point between the z axis and the bed surface; (4) setting an irradiating direction of the second sectorial laser beam so that, in the yz plane, the second sectorial laser beam passes through a first reference point indicated by a first marker disposed on the body surface at a first point of the chest of the subject to be inspected and also passes through a second reference point indicated by a second marker disposed on the body surface at a second point of the chest of the subject to be inspected; (5) moving the bed in the x direction so that the second sectorial laser beam irradiates the yz marking; and (6) moving the bed in the y direction so that the first sectorial laser beam passes through the first reference point in yz plane, thereby allowing the chest of the to-be-inspected subject to be disposed below the bottom of the cryostat in such a manner that a line joining the first and second reference points becomes coincident or parallel with one direction in which the centers of the SQUID sensors are arranged.

The above positioning method further comprises (7) moving the bed in the z direction until the irradiation point of the dot-like laser beam becomes coincident with the first reference-point; and (8) moving the bed in the z direction until the body surface of the subject to be inspected comes into contact with the bottom of the cryostat and determining the distance between the first reference point and the cryostat bottom. As the first and second points, the processus xiphoideus and incisura jugularis, respectively, of the subject to be inspected are used.

A typical biomagnetic field measuring method for the biomagnetic field measuring apparatus according to the present invention comprises (1) setting an irradiating direction of the first sectorial laser beam so that the first sectorial laser beam, which spreads sectorially in the xz plane, is applied to the xz marking; (2) setting an irradiating direction of the second sectorial laser beam so that the second sectorial laser beam, which spreads sectorially in yz plane, is applied to the yz marking; (3) setting an irradiating direction of the dot-like laser beam so that the dot-like laser beam, which is applied to the bed surface obliquely so as to intersect the first and second sectorial laser beams, irradiates a crossing line between the first and second sectorial laser beams and also irradiates a crossing point between the z axis and the bed surface; (4) setting an irradiating direction of the second sectorial laser beam so that, in the yz plane, the second sectorial laser beam passes through a first reference point indicated by a first marker disposed on the body surface of processus xiphoideus of the subject to be inspected and also passes through a second reference point indicated by a second marker disposed on the body surface of incisura jugularis of the subject to be inspected; (5) moving the bed in the x direction so that the second sectorial laser beam irradiates the yz marking; (6) moving the bed in the y direction so that the first sectorial laser beam passes through the first reference point in the yz plane; (7) moving the bed in the z direction until the irradiation point of the dot-like laser beam comes into coincidence with the first reference point; (8) moving the bed in the z direction until the body surface of the subject to be inspected comes into contact with the bottom of the cryostat, and determining the distance between the first reference point and the cryostat bottom; and, thereafter, (9) detecting a magnetic field generated from the heart of the subject to be inspected.

The chest of the subject to be inspected is disposed below the bottom of the cryostat so that a line joining the first and second reference points becomes coincident or parallel with one direction in which the centers of the SQUID sensors are arranged.

Embodiments of the present invention will be described in detail hereinafter with reference to the accompanying drawings.

First-Embodiment

Figure 2:
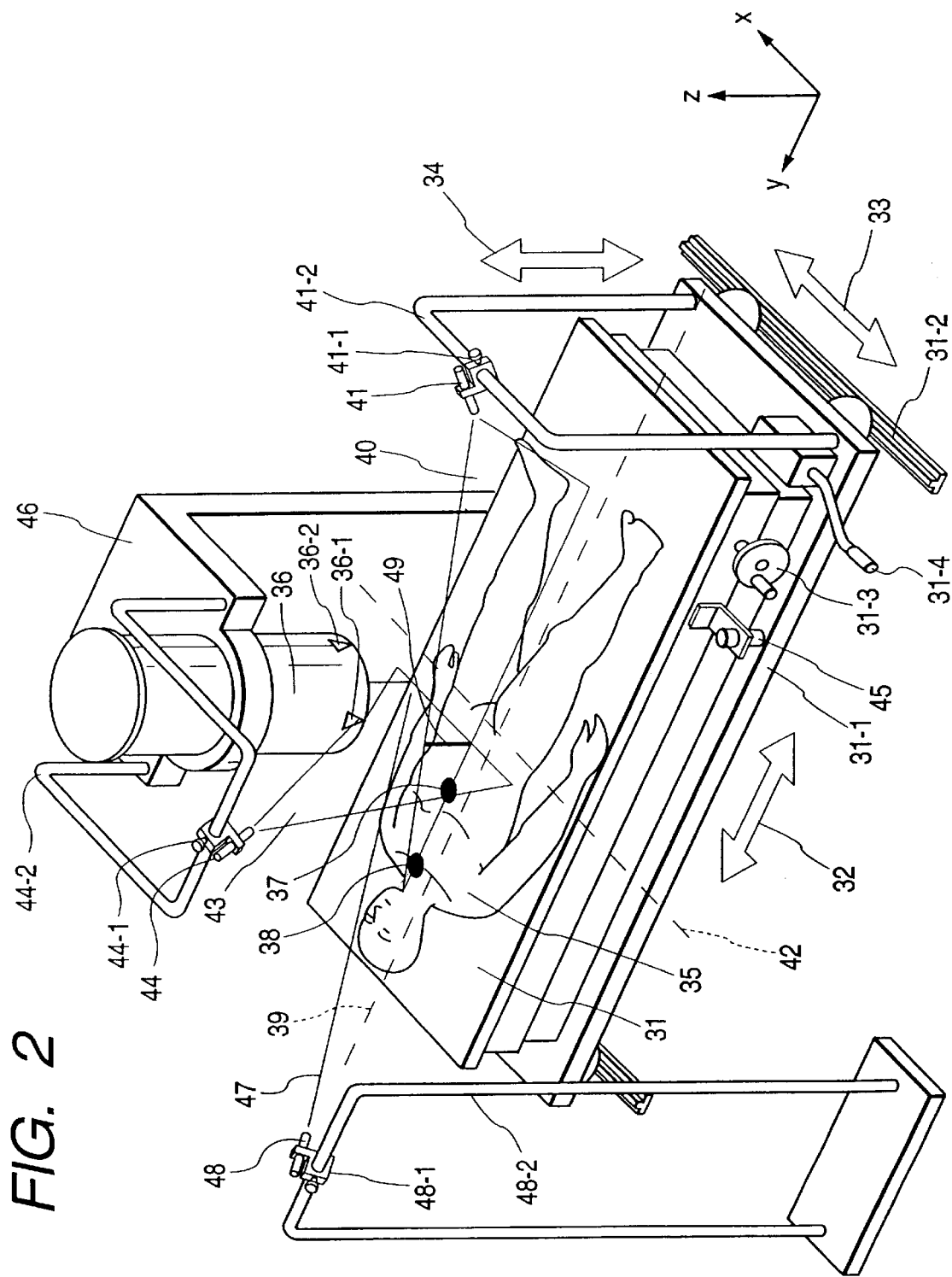
FIG. 2 is a perspective view which illustrates details the apparatus of FIG. 1.

FIG. 1 shows an example of the overall construction of a biomagnetic field measuring apparatus according to a first embodiment of the present invention, and FIG. 2 illustrates the details thereof. As shown in FIG. 1, in the interior of a magnetically shielded room 2, there are disposed a bed 31 on which a subject 35 to be inspected lies and a gantry 46 which holds a Dewar (cryostat) 36. Plural sensors (SQUID sensors) for detecting a magnetic field signal in the z direction (normal line direction) generated from a living booy are arranged near an inner bottom of the Dewar 36 in the x and y directions in a two-dimensional lattice shape (the plural sensors arranged in two dimensions are called a sensor array).

Figure 4:
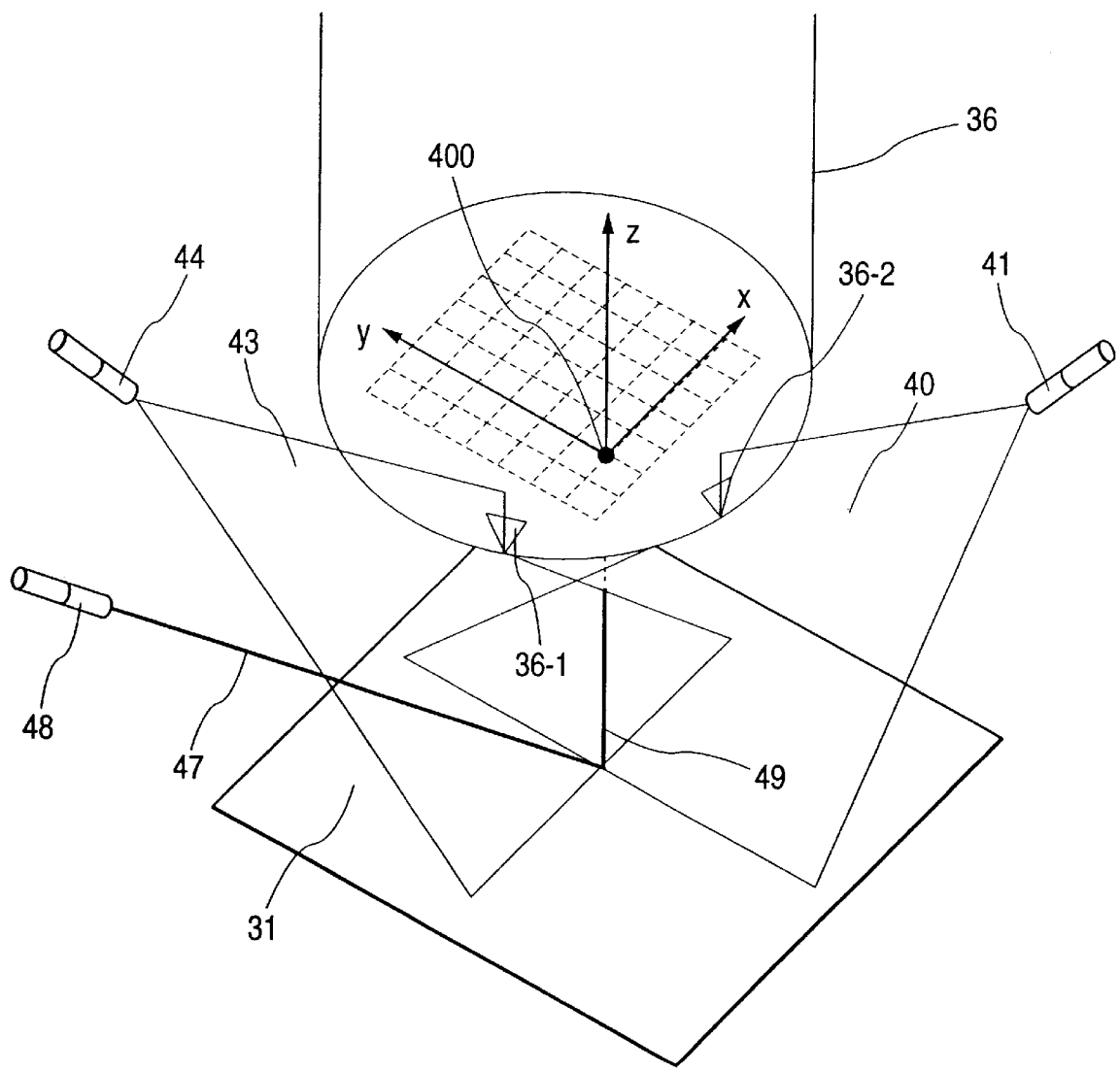
FIG. 4 is a diagram which illustrates the manner in which three laser beams are adjusted as to their irradiating directions, which laser beams are used in positioning the subject to be inspected below the lower surface of the Dewar.

As shown in FIG. 4, sixty-four SQUID sensors for detecting a very weak magnetic field generated from the heart of the subject to be inspected are arranged on an inner bottom of the cryostat (Dewar) 36 in two dimensions, respectively, at lattice points of an 8×8 square lattice. Each SQUID sensor is provided with a primary differential type pickup coil, including a pickup coil and a compensating coil, and detects a magnetic field in a normal line direction (z direction, perpendicular to the body surface).

The sensor array is driven by a driving circuit 6 and an output from the sensor array is amplified and filtered by an amplifier and filter unit 7 and is then received by a computer (a processing unit) 8.

The computer (processing unit) 8 performs an arithmetic operation for obtaining an average magnetic waveform or added magnetic waveform in the normal direction of the magnetic field generated from the heart and detected by the sensor array; and, thereafter from the average magnetic waveform or added magnetic waveform in the normal direction, the computer 8 determines a magnetic field component in a tangential direction of the magnetic field generated from the heart. Further, using the magnetic field component in the tangential direction, the computer 8 performs various arithmetic processings, such as analyzing a magnetic field distribution at coordinate points where plural sensors are arranged, preparing an isomagnetic field map by joining coordinate points equal in magnetic field intensity, preparing an arrow map which represents activated positions in the heart of the subject to be inspected as a two-dimensional current distribution, integrating a magnetic waveform in a temporary interval, including a specific period of the activity of the heart to determine an integral intensity, and preparing an isointegral map joining coordinate points equal in integral intensity, and estimating the position of a current source from a magnetic field component in the normal line direction. The computer 8 then displays the results of the processings on a display unit.

The method of determining a tangential magnetic field component from the magnetic field component in the normal line direction and the method of preparing an isomagnetic field map and an isointegral map, using the tangential magnetic field component, were developed for the first time by the present inventors and are publicly known techniques (see JP-A-No. Hei 10-305019).

If t is assumed to be a time constant, coordinates of SQUID sensors are assumed to be (x, y), and a measured magnetic field component in the normal line direction is assumed to be $B_z(x, y, t)$, then tangential magnetic field components $B_x(x, y, t)$ and $B_y(x, y, t)$ are obtained in accordance with the following equations (1) and (2):

$$B_x(x, y, t) = -\partial B_z(x, y, t)/\partial x \quad (1)$$

$$B_y(x, y, t) = -\partial B_z(x, y, t)/\partial y \quad (2)$$

As shown in FIG. 2, the biomagnetic field measuring apparatus of the first embodiment is provided with y-axis direction moving means for moving the bed, on which the subject 35 to be inspected is supported in a transverse direction (y-axis direction) 32, x-axis direction moving means for moving the bed in a longitudinal direction (x-axis direction) 33, and z-axis direction moving means for moving the bed in a vertical direction (z-axis direction) 34. The upper surface of the bed 31 is held in parallel with the bottom of the Dewar 36, i.e., the xy plane. The bed 31 is held on a bed support 31-1 and is movable in the x-axis direction 33 on feed rails 31-2 by operation of a longitudinal feed handle (not shown). The bed 31 is also movable in the y-axis direction 32 on the bed support 31-1 by operation of a transverse feed handle 31-3, and is further movable in the z-axis direction 34 on the bed support 31-1 by operation of an oil hydraulic pump handle 31-4.

In the biomagnetic field measuring apparatus according to the present invention, the spatial position of Dewar 36 is fixed, and, assuming that the measuring plane (401 in FIG. 5) is the xy plane, a coordinate system (x, y, z) of the biomagnetic field measuring apparatus is established wherein a centroid position of each coordinate point (x, y) in the pickup coil-containing sensors (SQUID sensors) (402 in FIGS.) is an origin (0, 0, 0). The position of a sensor located at a specific position of the sensor array may be established as the origin of the coordinate system (x, y, z). The sensors are arranged two-dimensionally like a lattice in x and y directions on the measuring plane (401 in FIG. 5) which is parallel to the bed 31. An xz marking 3-6-1 indicating an intersecting line between the xz plane of the coordinate system (x, y, z) and an outer peripheral side face of the lower portion of Dewar the 36 and a yz marking 36-2 indicating an intersecting line between the yz plane of the coordinate system and the outer peripheral side face are affixed to the said outer peripheral side face.

In the biomagnetic field measuring apparatus of the first embodiment, the subject 35 to be inspected on the bed 31 is to be disposed in a predetermined certain direction and at a predetermined certain position with respect to the bottom of Dewar 36, and, for this purpose, the apparatus is provided with a laser generator 41 for generating a sectorial laser beam 40 which spreads in a long axis direction 39 of the bed 31, a laser generator 44 for generating a sectorial laser beam 43 which spreads in a short axis direction 42 of the bed 31, a laser generator 48 for generating a dot-like laser beam 47 which intersects the z axis of the coordinate system (x, y, z) by changing its irradiating direction, and an ultrasonic displacement sensor 45 for measuring the displacement of the bed 31 from the floor surface. The spread angle of the laser beam 40, which is radiated sectorially to a plane parallel to the yz plane, and the spread angle of the laser beam 43, which is radiated sectorially to a plane parallel to the xz plane, can each be changed. An intersecting line 49 between the sectorial laser beams 40 and 43 is parallel to the z axis in the Coordinate system (x, y, z). The laser beams 40, 43, and 48 range in wavelength from 300 to 850 nm, which laser beams may be replaced by light beams generated from other light sources and ranging in wavelength from 300 to 850 nm.

The laser generator 41 is held by a generator holder 41-1, which in turn can be fixed to a pipe frame 41-2 so that the irradiating direction of the laser beam 40 can be changed and fixed to a specific direction (second position changing means), the pipe frame 41-2 being fixed to the bed support 31-1. Likewise, the laser generator 44 is held by a generator holder 44-1, which in turn can be fixed to a pipe frame 44-2 so that the irradiating direction of the laser beam 43 can be changed and fixed to a specific direction, the pipe frame 44-2 being fixed to a gantry 46. Thus, the generator holder 41-1 is movable in the x-axis direction 33 on the pipe frame 41-2 and is tiltable around the axis of the pipe frame 41-2 (first position changing means).

Likewise, the generator holder 44-1 is movable in the y-axis direction 32 on the pipe frame 44-2 and is tiltable around the axis of the pipe frame 41-2. The pipe frame 41-2 is fixed to the bed support 31-1 on the foot side of the human body supported on the bed 31 so that light ranging in wavelength from 300 to 850 nm may not enter the person's eyes. The pipe frame 44-2 overhangs horizontally at a higher position than the position of the Dewar 36.

The laser generator 48, which is held by a generator holder 48-1, can be fixed to a pipe frame 48-2 so that the irradiating direction of the dot-like laser beam 47 is changeable and is a specific direction, the pipe frame 48-2 being fixed to any of the floor surface, ceiling, and wall surface. The generator holder 48-1 is movable in the y-axis direction on the pipe frame 48-2 and is tiltable around the axis of the pipe frame 48-2. The pipe frame 48-2 is fixed to the inner floor surface or wall surface of the magnetically shielded room.

For measuring a magnetic field generated from the heart of the subject 35 to be inspected, the subject 35 is disposed at a predetermined certain position in a predetermined certain direction in the coordinate system (x, y, z) with respect to the bottom of Dewar 36. For example, the subject 35 to be inspected is disposed in such a manner that substantially the whole of the projection of the heart on the sensor array surface is positioned within the region of the sensor array, and that the chest surface of the subject 35 comes into contact with the lower surface of the Dewar 36. This operation will be described below with reference to FIGS. 3 and 4.

Figure 3:
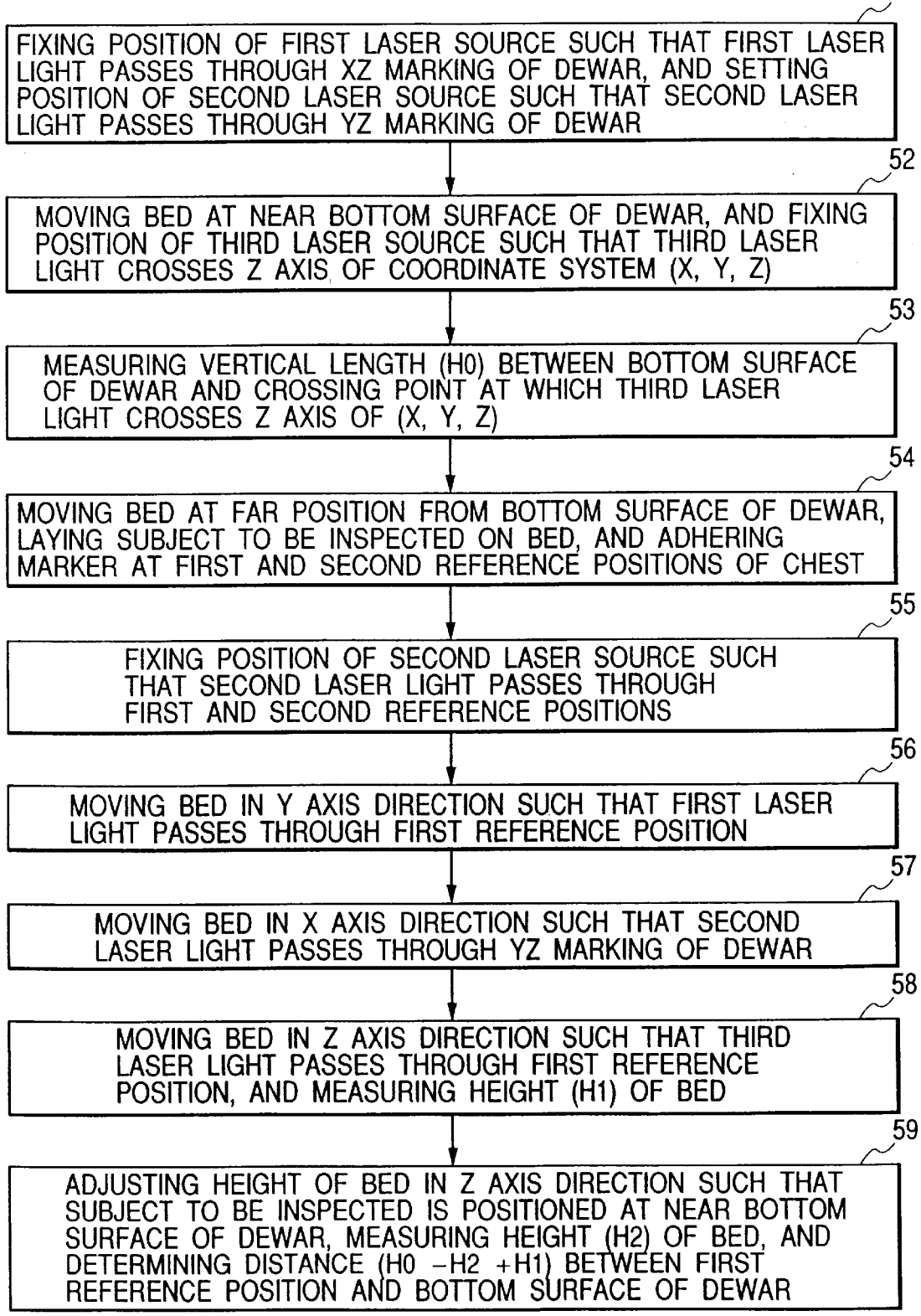
FIG. 3 flow diagram which shows schematically an example of the procedure used when a subject is laid on a bed for inspection below a lower surface of a Dewar.

FIG. 3 is a schematic diagram showing an example of the procedure in which the subject to be inspected is disposed on the bed and below the Dewar in the first embodiment of the present invention, and FIG. 4 illustrates how to adjust the irradiating directions of the three laser beams which are used in positioning the subject to be inspected on the bed and below the Dewar.

In the first embodiment, in order for substantially the whole of the projection of the heart on the xy plane to be positioned within the region of the sensor array, an adjustment is made so that the z axis in the coordinate system (x, y, z) passes through a preset sensor position. more specifically, the position of the subject to be inspected is adjusted with respect to the sensor array so that the processus xiphoideus of the subject to be inspected is aligned with the z axis, thereby allowing substantially the whole of the projection of the heart on the sensor array surface to be positioned within the region of the sensor array.

Step 1 (reference numeral 51): First, the bed 31 is moved in the x and/or y direction and is thereby positioned below the Dewar 36. Next, the bed 31 is moved in the z-axis direction 34 to set an upper surface of the bed at a position higher than the body surface height of the subject 35 to be inspected, which height has been measured with the bed adjusted to its lowest height. At this time, the height HL of the bed 31 from the floor surface is measured by means an ultrasonic displacement sensor 45, which may be replaced by a commonly-used sensor (distance measuring means), e.g., an optical displacement sensor. The height of the bed 31 from the floor surface corresponds to the distance between the upper surface of the bed and the floor surface or the distance between the position of the displacement sensor and the floor surface, the displacement sensor being mounted in a suitable position of the bed 31 in the z-axis direction 34 at a certain distance from the bed upper surface and being moved together with the bed upper surface by the z-axis direction moving means in the z-axis direction 34.

The position of the generator holder 44-1 is moved on the pipe frame 44-2 to change, as necessary, the spread angle of the laser beam 43 (the first sectorial laser beam) which is generated from the laser generator (the first laser source) 44 and which spreads sectorially in a plane parallel to the xz plane, and at a position where the laser beam 43 passes through the xz marking 36-1 affixed to a lower outer peripheral side face of the Dewar 36 and irradiates the upper surface of the bed 31, the position of the generator holder 44-1 is fixed to the pipe frame 44-2.

Likewise, the position of the generator holder 41-1 is moved on the pipe frame 41-2 to change, as necessary, the spread angle of the laser beam 40 (the second sectorial laser beam), which is generated from the laser generator (the second laser source) 41 and which spreads sectorially in a plane parallel to the yz plane; and, at a position where the laser beam 40 passes through the yz marking 36-2 affixed to a lower outer peripheral side face of the Dewar 36 and irradiates the upper surface of the bed 31, the position of the generator holder 41-1 is fixed to the pipe frame 41-2. The sectorial laser beams 40 and 43 intersect each other to form an intersecting line 49 which is parallel to the z axis in the coordinate system (x, y, z).

FIG. 4 illustrates in what manner the three laser beams are adjusted as to their irradiating directions in step 2, which will be described below.

Step 2 (reference numeral 52): By moving the generator holder 48-1 in the y-axis direction 32 on the pipe frame 48-2 and by tilting it around the axis of the pipe frame 48-2, the irradiating direction of the dot-like laser beam (the third laser) 47 generated from the laser generator (the third laser source) 48 is changed, and the generator holder 48-1 is fixed to the pipe frame 48-2 at a position such that, on the surface of the bed 31, the laser beam 47 intersects the intersecting line 49 which is parallel to the z axis of the coordinate system (x, y, z). That is, first the position of the generator holder 48-1 is set so that the laser beam 47 irradiates the xz marking 36-1, and, thereafter the generator holder 4&z1 is tilted around the axis of the pipe frame 48-2 and the position of the generator holder 48-1 is fixed so that the laser beam 47 and the intersecting line 49 intersect each other on the bed surface (the third position changing means).

Step 3 (reference numeral 53): With the ultrasonic displacement sensor 45, a determination is made of a vertical distance H0 between an intersecting point of the laser beam 47 and the intersecting line 49 on the surface of the bed 31 and the lower surface of the Dewar 36. The bed 31 is moved in the z-axis direction so that the surface thereof comes into contact with the lower surface of the Dewar 36, and the height HH of the bed from the floor surface is measured by the ultrasonic displacement sensor 45. H0 is equal to (HH–HL).

Step 4 (reference numeral 54): The bed 31 is moved in the x-axis direction 31 up to a position where the bed is spaced sufficiently away from a projected position of the Dewar 36 on the floor and where the Dewar 36 is not an obstacle to placing the to-be-inspected subject 35 on the bed. Then, the bed 31 is moved in the z-axis direction and is set at a low height. The subject 35 to be inspected is laid onto the bed in such a manner that the body axis direction thereof becomes almost parallel to the long axis direction 39 of the bed 31. Two (first and second) reference points 37 and 38 are provided on the chest surface along the body axis of the subject 35 to be inspected.

For example, as the position of the reference point 37, there is selected the position of processus xiphoideus (the first reference point), and as the position of the reference point 38, there is selected the position of incisura jugularis (the second reference point). The body surface positions of processus xiphoideus and incisura jugularis can be determined easily by touch and can be used as reference points. Markers, which will be described later, are affixed respectively to the reference points 37 and 38.

Step 5 (reference numeral 55) The generator holder 41-1 is moved on the pipe frame 41-2 to change the irradiating direction of the laser beam 40 which is generated from the laser generator 41 and which spreads sectorially in a plane parallel to the yz plane, and the generator holder 41-1 is moved on the pipe frame 41-2 so that the laser beam 40 passes through the centers of the reference points 37 and 38, and/or the subject 35 to be inspected is moved on the bed 31. As a result, the line passing through the reference points 37 and 38 becomes parallel to the long axis direction 39 of the bed 31, and the generator holder 41-1 is fixed to the pipe frame 41-2 at a position where the sectorial laser beam 40 passes through the centers of the reference points 37 and 38.

Step 6 (reference numeral 56): The spread angle of the sectorial laser beam 43 generated from the laser generator 44 is changed, as necessary, and the bed 31 is moved in the y-axis direction 32 so that the laser beam 43 passes through the center of the reference point 37. As a result, the intersecting line 49 of a cross beam pattern between the laser beams 40 and 43 and the center of the reference point 37 are aligned with each other. In this state, the movement of the bed 31 in the y-axis direction 32 is locked.

Step 7 (reference numeral 57): The spread angle of the laser beam 40 generated from the laser generator 41 is changed, as necessary, and the bed 31 is moved in the x-axis direction 33 so that the laser beam 40 passes through the yz marking 36-2 affixed to the lower outer peripheral side face of the Dewar 36. The movement of the bed 31 in the x-axis direction is locked at the position where the laser beam 40 passes through the yz marking 36-2. As a result, there is realized a state in which the z axis of the coordinate system (x, y, z) passes through the center of the reference point 37.

Step 8 (reference numeral 58): The bed 31 is moved in the z-axis direction so that the laser beam 47 passes through the center of the reference point 37; and, thereafter, the height H1 of the bed 31 from the floor surface is measured by the ultrasonic displacement sensor 45. Consequently, irrespective of the body shape of the subject 35 to be inspected, the vertical distance between the reference point 37 and the Dewar 36 can be set always at HO=(HH−HL).

Step 9 (reference numeral 59): Lastly, the bed 31 is moved in the z-axis direction 34, allowing the chest surface of the subject 35 to be inspected to approach the lower surface of the Dewar 36 so that there can be obtained a large signal output. Next, the height H2 of the bed 31 from the floor surface is measured by the ultrasonic displacement sensor 45. A vertical distance H3 between the reference point 37 and the bottom of the Dewar 36, in an approximated state of the chest surface of the subject 35 to be inspected, to the lower surface of Dewar is H3={HO−(H2−H1)}, which will be different depending on the body shape of the subject to be inspected.

By thus using the reference points 37 and 38 and the three laser sources, substantially the whole of the projection of the heart on the sensor array surface is positioned within the region of the sensor array, and the chest surface of the subject 35 to be inspected comes into contact with the lower surface of Dewar 36, thereby allowing a large signal output to be obtained, and these operations can be done in a short time and easily.

In obtaining a morphological image by an MRI device, the center of MRI marker is located at the same chest position as the central position of the reference point 37, the body shaft is brought into alignment with the long axis of the bed 31 in the MRI device, and plural tomograms parallel to and different in depth from the bed surface are photographed. Of course, these plural tomograms include a tomogram with an MRI marker being photographed.

Figure 5:
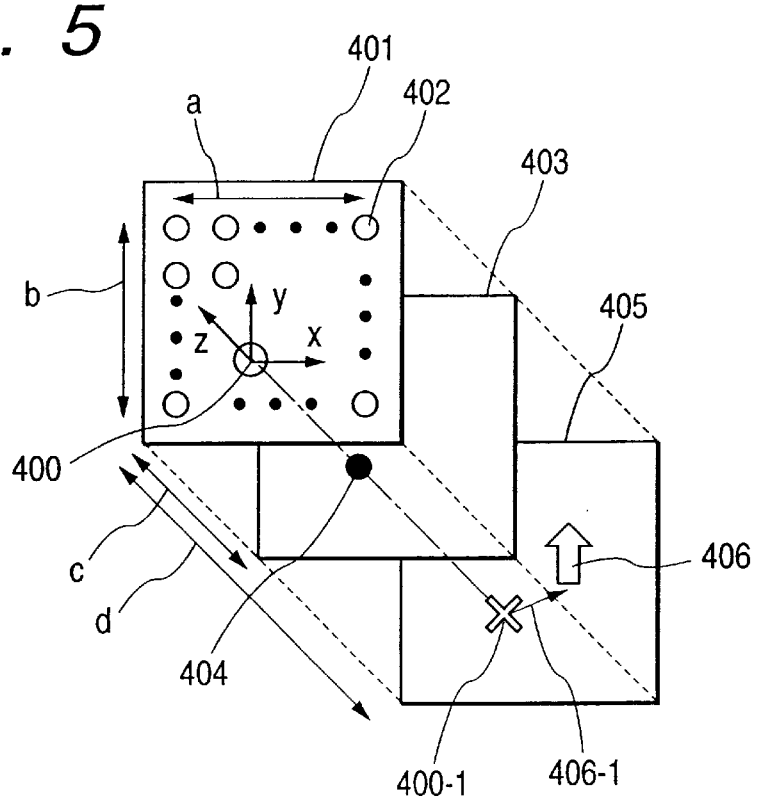
FIG. 5 is a diagram which shows a display example of information obtained by the biomagnetic field measuring apparatus of the first embodiment, showing an image which represents an estimated active position.

FIG. 5 shows a display example of information obtained by measurement and analysis using the biomagnetic field measuring apparatus of the first embodiment. In the example shown in FIG. 5, the origin of the coordinate system (x, y, z) is set at the position of a sensor 400, located at a specific position, out of plural sensors 402 disposed in a measuring plane 401 which is parallel to the bed 31; the reference point 37 is affixed to a processus xiphoideus position 404 of the subject 35 to be inspected; the subject 35 to be inspected is disposed so that the processus xiphoideus 404 passes through the z axis of the coordinate system, and a magnetic field generated from the heart is measured. The results of these operations are shown in the example of FIG. 5. According to these results, as seen in FIG. 5, the processus xiphoideus 404 lies in a plane 403 which is parallel to the measuring plane 401 and which is present at a depth of c, and an active position 406 indicated with an open arrow mark has been specified at a tip posit-ion of a solid line arrow 406-1 from an intersecting point (open X mark) 400-1 between a plane 405 parallel to the measuring plane 401 and present at a depth of d and the z axis of the coordinate system.

A vertical distance H4 between the measuring plane 401 and the lower surface of Dewar 36 is known and the depth c from the measuring plane 401 to processus xiphoideus 404 is c=(H3+H4)={HO−(H2−H1)+H4}.

In the example shown in FIG. 5, as in FIG. 4, there is established a coordinate system (x, y, z) wherein the z axis passes through the position of processus xiphoideus and further passes through the position of a sensor located at a specific position in the sensor array. It is well known that the position of a current source, i.e., an active position, can be estimated by any of various analyzing methods which estimate a current source.

An image which represents whether an estimated active position is present or not is provided with plural pixels having coordinates corresponding to SQUID sensors arranged two-dimensionally in x and y directions like a lattice. In an image formed in a plane of a depth (z) where an estimated active position is present, a current source magnitude is imparted to the pixel of coordinates (x, y) at the estimated active position, while zero is imparted to the pixel of coordinates (x, y) estimated free of any active position. Alternatively, as in the example of FIG. 5, and also in the example of FIG. 7, which will be referred to later, open arrow mark data representing both direction and magnitude of the current source may be imparted to the estimated position of the active position 406.

Given that, on the display screen of the display unit of the biomagnetic field measuring apparatus, the magnitude in the x direction of the image representing the estimated active position is a, and that in the y direction it is b (FIG. 5), the number of pixels in the x direction and in y direction are n, and n, respectively, and the pixel magnitude in the x direction and in y direction are $\Delta x$ and $\Delta y$, respectively, $a=n_x\Delta x$ and $b=n_y\Delta_y$. If the measuring region with SQUID sensors arranged two-dimensionally in x and y directions like a lattice is assumed to be $P_x$ and $P_y$, the photographing magnifications in the x and y directions of the image obtained by the biomagnetic field measuring apparatus are $(a/P_x)$ and $(b/P_y)$, respectively.

Figure 6:
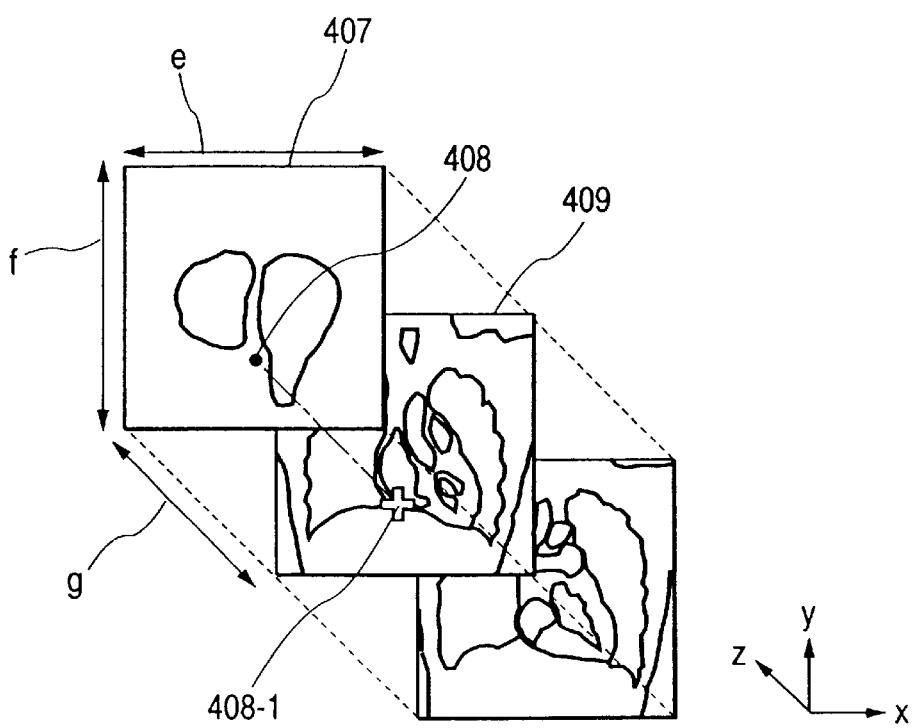
FIG. 6 is a diagram which shows a display example, indicating the position of a tomogram obtained by an MRI device and which is to be combined with an image indicative of an estimated active position obtained by the biomagnetic field measuring apparatus of the first embodiment.

FIG. 6 shows a display example indicating the position of a tomogram (a morphological image) obtained by an MRI device and which is to be combined with an image indicative of an estimated active position, the image being obtained by the biomagnetic field measuring apparatus in the first embodiment. Plural tomograms including a tomogram with an MRI marker photographed are displayed on the display unit of the biomagnetic field measuring apparatus.

With the MRI device, it is possible to photograph a tomogram 407 which includes an MRI marker 408 disposed at the reference point 37 and which is parallel to the bed surface, as well as a plurality of tomograms parallel to and different in depth (z) from the tomogram 407.

It is here assumed that the magnitude in the x direction of a tomogram image obtained by the MRI device and the magnitude in y direction are e and f, respectively, (FIG. 6), the number of pixels in the x direction and in y direction are $N_x$ and $N_y$, respectively, and the pixel magnitude in the x direction and in y direction are $\Delta x$ and $\Delta y$, respectively. If a tomogram photographing region by the MRI device is assumed to be defined by $Q_x$ and $Q_y$, the photographing magnification in the x direction of the tomogram is $(e/Q_x)$, and that in the y direction is $(f/Q_y)$. Thus, $e=N_x\Delta X$, $f=N_y\Delta Y$.

For combining an image obtained by the biomagnetic field measuring apparatus of the first embodiment and representing an estimated active position with a morphological image obtained by the MRI device, it is necessary to extract a tomogram 409 at a depth of g corresponding to the distance (d-c) in FIG. 5 from among plural tomograms parallel to the tomogram 407 and different in depth. The tomogram 409 at depth g is the $\{(d-c)/L\}^{th}$ tomogram from the tomogram 407 if the tomogram thickness is assumed to be L. In FIG. 6, an open+mark 408-1 indicates the position of the processus xiphoideus in the tomogram 409.

Figure 7:
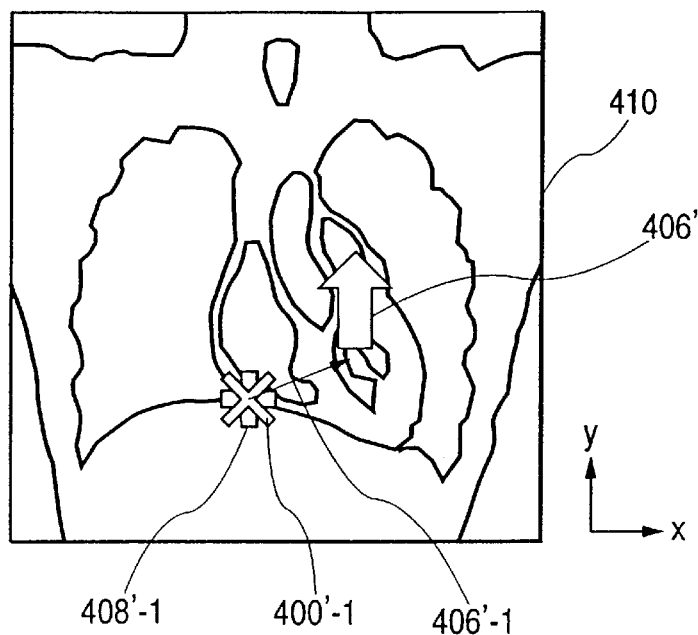
FIG. 7 is a diagram which shows a display example of a combined image of an image indicative of an estimated active position obtained by the biomagnetic field measuring apparatus of the first embodiment and a tomogram obtained by an MRI device.

FIG. 7 shows a display example of an image on the display unit of the biomagnetic field measuring apparatus in the first embodiment, wherein there is illustrated a combined image of an image obtained by the biomagnetic field measuring apparatus and representing an estimated active position with a morphological image (tomogram) obtained by the MRI device. Such a combined image is formed in accordance with the following procedure.

First, for combining the two images, it is necessary that the photographing magnification of the image 405, which represents an estimated active position, and that of the tomogram 407 be made equal to each other. That is, it is necessary that the two images be made equal in pixel size.

Since $a=n_x\Delta x$, $b=n_y\Delta y$, $e=N_x\Delta X$, and $f=N_y\Delta Y$, the pixel size $\Delta x$, $\Delta y$ of the image 405 can be made equal to the pixel size $\Delta X$, $\Delta Y$ of the tomogram by multiplying $\Delta x$ by $(\Delta X/\Delta x)$ and multiplying $\Delta y$ by $(\Delta Y/\Delta y)$. More specifically, an image 405' is formed by multiplying the pixel size $\Delta x$ of the image 405 in x direction by $\{(e/a) (n_x/N_x)\}$ and multiplying the pixel size $\Delta y$ thereof in y direction by $\{(f/b) (n_y/N_y)\}$. At this time, the size in x direction of the image 405' is $\{e (n_x/N_x)\}$ and that in y direction is $\{f (n_y/N_y)\}$.

Generally, $n_x \neq N_x$ and $n_y \neq N_y$ and the reference point position in the image 405' and the central position of MRI marker in the tomogram 407 are different from each other, so for combining the image 405' with the tomogram 407, there is performed a processing for making the reference point position and the central position of the MRI marker coincident with each other between the two images, and consideration is given to only the pixels of the image 405' that are lapped with the tomogram 407.

Next, the image 405' is superimposed on the tomogram 407 so that the central position of the MRI marker 408 and the central position of the reference point 37 [the position (x, y) of processus xiphoideus 404 in the coordinate system (x, y, z) of the biomagnetic field measuring apparatus] become coincident with each other.

At this time, data on the tomogram 407 and data on the image 405' are stored in memory in a corresponding relation to each other and at the same time data on plural tomograms parallel to the tomogram 407 are also stored in memory corresponding to the data on the image 405'. The central position of the MRI marker 408 in the tomogram 407 is projected on the plural tomograms parallel to the tomogram 407 and is stored in memory.

Next, the image 405' including an open arrow mark indicative of the active position 406, as well as the tomogram 409, are read out from the memory and are made into a single sheet of image data. In this way, there is formed a combined image 410. The position of an open x mark 400'-1 obtained by enlarging an open x mark 400-1 in FIG. 5 and the position of an open+mark 408'-1 obtained by enlarging an open+mark 408-1 in FIG. 6 are displayed in an overlapped state, and there is displayed the combined image 410 which includes an arrow 4061-1 obtained by enlarging the arrow 406-1 in FIG. 5, an open arrow mark 406' obtained by enlarging the open arrow mark of the active position 406 in FIG. 5, and the tomogram. For example, in displaying the combined image, the image 405' and the tomogram 409 are displayed in different colors.

According to the combined image preparing method described above, since the central position of the MRI marker 408 is projected on the plural tomograms parallel to the tomogram 407 in the memory, it is possible to easily combine the image 405' with a tomogram other than the tomogram 409, thus permitting easy understanding of a relative positional relation between various portions of the heart and the active position 406. In the case where plural active positions 406 are detected, the processing described above may be executed for each of such plural active positions 406.

The tomogram obtained above, as a morphological image produced by an MRI device, may be replaced by a tomogram obtained by an MRI device and representing a blood flowing state.

Second Embodiment

Figure 8:
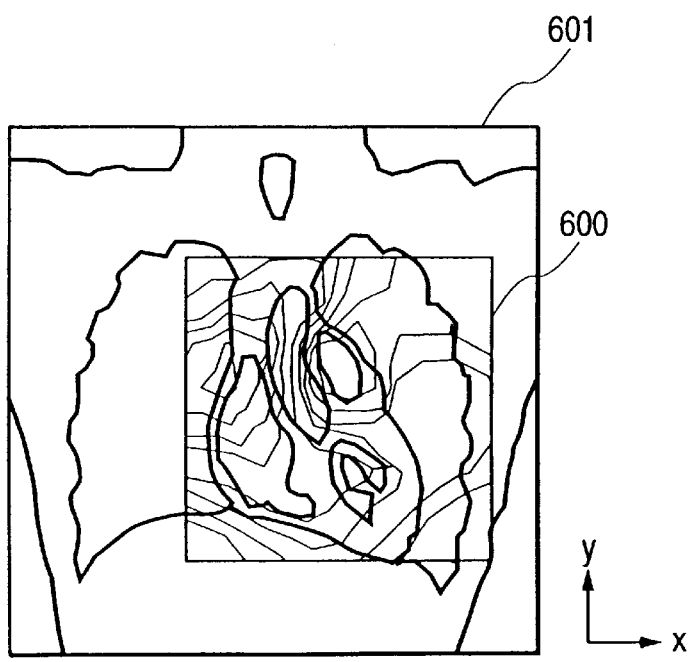
FIG. 8 is a diagram which shows a display example of a combined image of an isomagnetic field map obtained by a biomagnetic field measuring apparatus with a tomogram obtained by an MRI device, according to the second embodiment of the present invention.

FIG. 8 shows a display example of an image on a display unit of a biomagnetic field measuring apparatus according to the second embodiment of the present invention, in which there is illustrated a combined image 601 of an isomagnetic field map obtained by the biomagnetic field measuring apparatus with a tomogram (a morphological image) obtained by an MRI device. In the same way as in the first embodiment there are performed a processing for making the pixel size of an image representative of the isomagnetic field map coincident with the pixel size of the tomogram, and a processing for making a central position of a reference point in the isomagnetic field map [corresponding to the position of a measuring plane through which the z axis in a coordinate system (x, y, z) of the biomagnetic field measuring apparatus passes] coincident with a reference point (a central position of an MRI marker image).

By replacing the image 405 in the first embodiment with an isomagnetic field map, wherein points equal in magnetic field intensity measured at a certain time by plural SQUID sensors are connected together, it is possible to select an arbitrary tomogram from plural tomograms parallel to the tomogram 407 shown in FIG. 6, and then prepare a combined image 601 of the thus-selected tomogram with the isomagnetic field map and display the combined image on a display unit.

In FIG. 8, thick lines represent the tomogram obtained by the MRI device, while thin lines represent the isomagnetic field map in a measuring region 600 of the biomagnetic field measuring apparatus. Various contents can be displayed on the display screen of the display unit. For example, it is possible to change the depth of the tomogram successively, then select and designate a tomogram with a mouse or the like, and display a combined image of the tomogram with an isomagnetic field map, thus producing a display at each of plural different depth positions. It is also possible to display a combined image of an ever-changing isomagnetic field map with a tomogram selected from plural tomograms by means of a mouse or the like.

Since an ever-changing isomagnetic field map can be displayed superimposedly on the selected tomogram, significant diagnostic information can be obtained by comparison between morphological information represented by the tomogram and the state of change of the isomagnetic field map, which is functional information.

Figure 9:
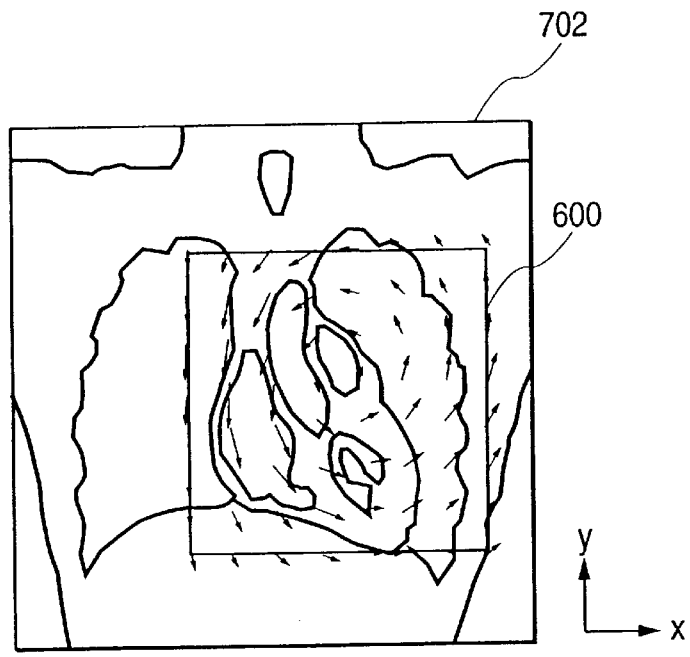
FIG. 9 is a diagram which shows a display example of a combined image of an arrow map obtained by the biomagnetic field measuring apparatus with a tomogram obtained by the MRI device in the second embodiment.

FIG. 9 shows a display example of am image on the display unit of the biomagnetic field measuring apparatus in the second embodiment, in which there is illustrated a combined image 702 of an arrow map obtained by the biomagnetic field measuring apparatus with a tomogram (a morphological image) obtained by an MRI device. In the example shown in FIG. 9, the isomagnetic field diagram in FIG. 8 is replaced by an arrow map which displays an activated position of the heart of the subject to be inspected as a two-dimensional current distribution.

In FIG. 9, thick lines indicate a tomogram obtained by the MRI device and arrows represent an arrow map. As in FIG. 8, various contents can be displayed on the display screen of the display unit. For example, changes with time of the arrow map can be displayed together with the selected tomogram.

Figure 10:
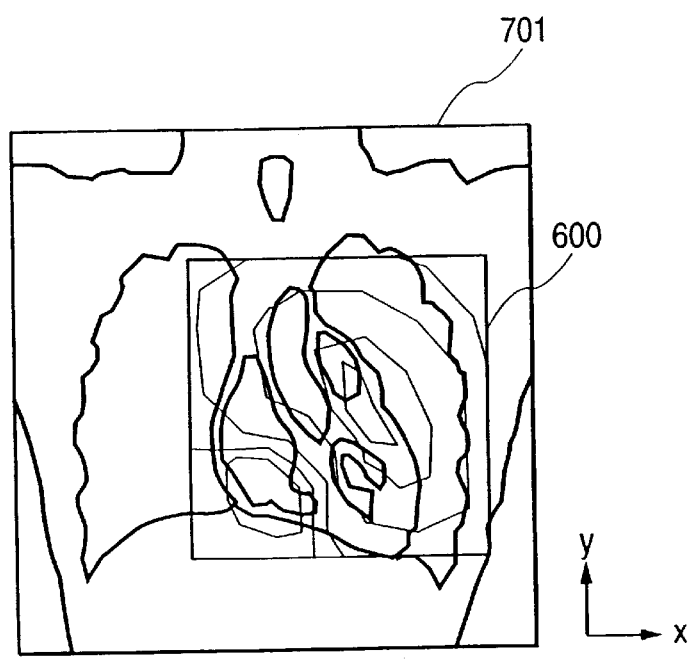
FIG. 10 is a diagram which shows a display example of a combined image of an isointegral map obtained by the biomagnetic field measuring apparatus with a tomogram obtained by the MRI device in the second embodiment.

FIG. 10 shows a display example of an image on the display unit of the biomagnetic field measuring apparatus, in which there is illustrated a combined image 701 of an isointegral map obtained by the biomagnetic field measuring apparatus with a tomogram (a morphological image) obtained by an MRI device. In the example shown in FIG. 10, the isomagnetic field map is replaced by an isointegral map prepared by integrating a magnetic waveform in a temporal interval including a specific period of the heart activity and connecting coordinate points equal in integral intensity, or an isointegral map prepared by integrating magnetic waveforms of tangential magnetic field components in a temporal interval, including two different periods, to obtain integral intensities and connecting coordinate points equal in the value of the difference between integral intensities in the temporal interval including two different periods.

In FIG. 10, thick lines indicate the tomogram obtained by the MRI device, while thin lines represent the isointegral map. As in FIG. 8, various contents can be displayed on the display screen of the display unit. For example, the isointegral map can be displayed together with tomograms at plural different depth positions.

Figure 11:
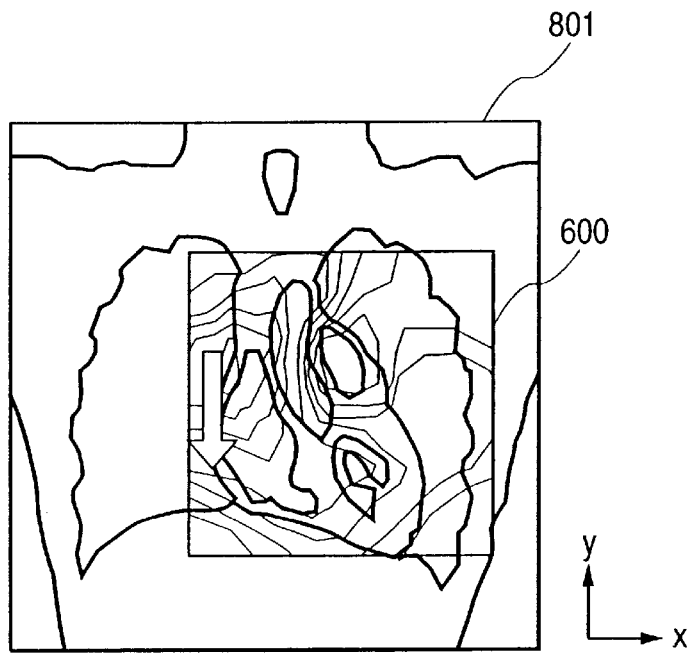
FIG. 11 is a diagram which shows a display example of a combined image of an activated position and an isomagnetic field map both obtained by the biomagnetic field measuring apparatus with a tomogram obtained by the MRI device in the second embodiment.

FIG. 11 shows a display example of an image on the display unit of the biomagnetic field measuring apparatus in the second embodiment, in which there is illustrated a combined image 801 of an activated position and an isomagnetic field map, both obtained by the biomagnetic field measuring apparatus with a tomogram (a morphological image) obtained by an MRI device. The combined image shown in the example of FIG. 11 is formed of three images, which include an isomagnetic field map, an image representing an activated position, and a tomogram obtained by the MRI device. The activated position is indicated by the direction and length of an open arrow mark. A tomogram including the activated position is displayed together with the isomagnetic field map and the activated position. In FIG. 11, thick lines indicate the tomogram obtained by the MRI device, while thin lines represent the isomagentic field map. As in FIGS. 8 and 9, various contents can be displayed on the display screen of the display unit. For example, there can be displayed a combined image formed of three images, which includes an ever-changing isomagnetic field map, a tomogram, and an activated position.

Figure 12:
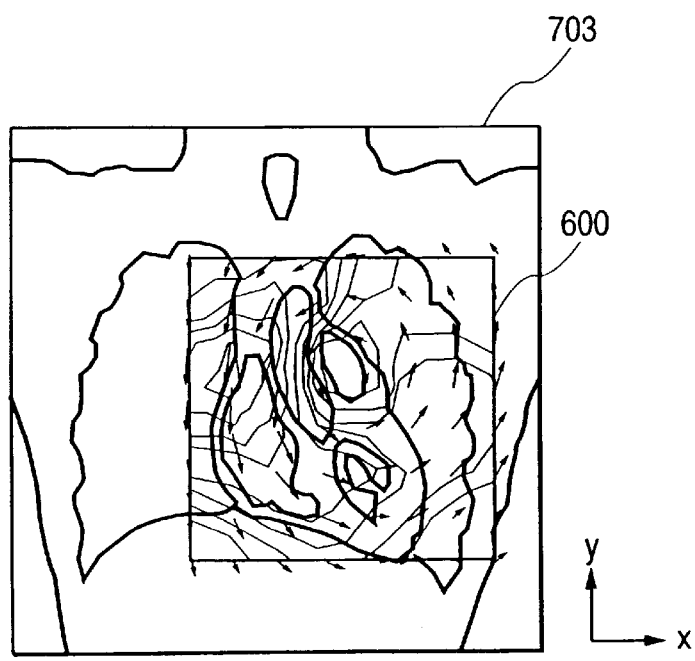
FIG. 12 is a diagram which shows a display example of a combined image of an isomagnetic field map and an arrow map both obtained by the biomagnetic field measuring apparatus with a tomogram obtained by the MRI device in the second embodiment.

FIG. 12 shows a display example of an image on the display unit of the biomagnetic field measuring apparatus in the second embodiment, in which there is illustrated a combined image 703 of an isomagnetic field map and an arrow map, both obtained by the biomagnetic field measuring apparatus with a tomogram (a morphological image) obtained by an MRI device. The example shown in FIG. 12 is of a combined image formed of three images, which include an isomagnetic field map, an arrow map, and a tomogram obtained by the MRI device. In the same example, the arrow map, which represents an activated position as a two-dimensional current distribution, is displayed together with the isomagnetic field map. In FIG. 12, thick lines indicate the tomogram obtained by the MRI device, thin lines represent the isomagnetic field map, and arrows represent the arrow map. As in FIGS. 8, 9 and 10, various contents can be displayed on the display unit. For example, there can be displayed a combined image formed of three images, which include an ever-changing isomagnetic field map, a tomogram, and an arrow map.

In the example shown in FIG. 8, there may be displayed a combined image formed of four images, which include an image representative of an activated position, an isomagnetic field map, an arrow map, and a tomogram obtained by the MRI device. Further, in the examples shown in FIGS. 8, 9, 10, 11, and 12, the tomogram (morphological image) obtained by the MRI device may be replaced by a tomogram obtained by an MRI device and representing a blood flowing state.

Third Embodiment

Figure 13:
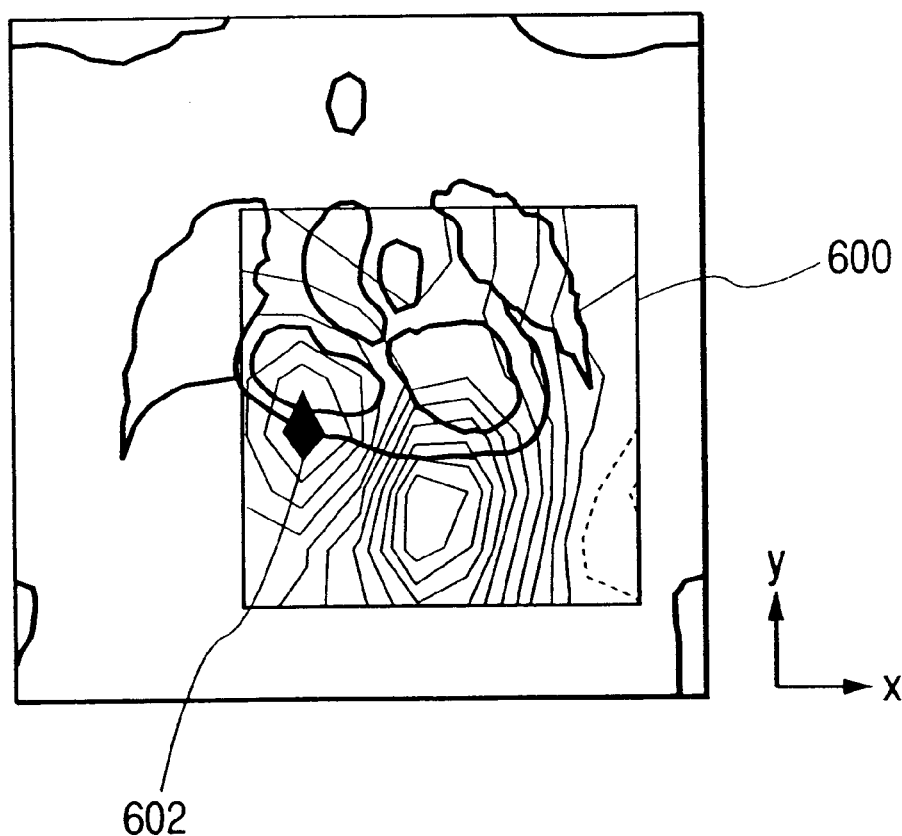
FIG. 13 is a diagram which shows a display example of a combined image of an isointegral map measured actually from a patient by a biomagnetic field measuring apparatus with a tomogram obtained by an MRI device, according to the third embodiment of the present invention.
Figure 14A:
FIGS. 14A to 14F are diagrams which show display examples of combined images each of an isomagnetic field map and an arrow map both measured actually from a patient by a biomagnetic field measuring apparatus with a tomogram obtained by an MRI device, according to the fourth embodiment of the present invention.
Figure 14D:
Figure 14B:
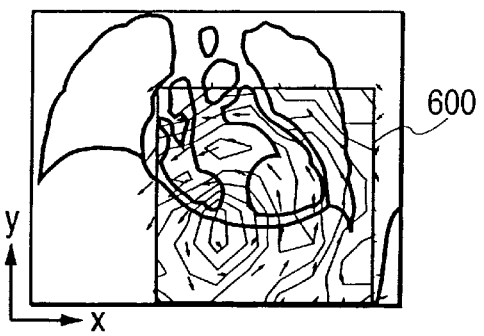
Figure 14E:
Figure 14C:
Figure 14F:

FIG. 13 shows a display example of an image formed on a display unit of a biomagnetic field measuring apparatus according to the third embodiment of the present invention, in which there is illustrated a combined image of an isointegral map obtained by measurement actually on a patient with use of the biomagnetic field measuring apparatus and a tomogram (a morphological image) obtained by an MRI device. The combined image is prepared in the same way as in the previous first and second embodiments.

In the example shown in FIG. 13, there is an isointegral map obtained by integrating magnetic waveforms in a temporal interval, including a period in which a QRS wave of the heart activity appears, and also including a period in which a T wave appears. Then, coordinate points equal in the value of the difference between integral intensities in the said time interval are connected.

In FIG. 13, thick lines indicate the tomogram obtained by the MRI device, while thin lines represent the isointegral map, the isointegral map being displayed together with the tomogram which has been selected from plural tomograms. In the same figure, an inactive position 602 of a cardiac muscle activity in the patient's heart is represented by a solid black portion. In the inactive position 602, the integral intensity is negative. The detection of such an inactive position of the cardiac muscle is considered to be very effective in the diagnosis of myocardial ischemia, such as angina pectoris and myocardial infarction.

Fourth Embodiment

FIG. 14 shows a display example of an image on a display unit of a biomagnetic field measuring apparatus according to the fourth embodiment of the present invention, in which there is illustrated a combined image of an isomagnetic field map and arrow map, both obtained by measurement actually on a patient with use of the biomagnetic field measuring apparatus and a tomogram obtained by an MRI device. The patient in FIG. 13 and the patient in FIG. 14 are different. The combined image is prepared in the same way as in the preceding first and second embodiments.

In the example shown in FIG. 14, there are an isomagnotic field map, wherein coordinate points equal in magnetic field intensity of a tangential magnetic field component derived from a magnetic field component in the normal line direction as measured in a period of P wave appearance of the heart activity are connected together, as well as an arrow map.

In FIG. 14, thick lines indicate the tomogram obtained by the MRI device, thin lines represent the isomagnetic field map in a measuring region 600, and arrows represent the arrow map. FIGS. 14A to 14F show actual measurement examples of changes with time of the isomagnetic field map displayed on the display screen of the display unit, in which the isomagnetic field diagram is displayed together with one tomogram having been selected from plural tomograms. The isomagnetic field maps shown in those figures each correspond to the lapse of time every 25 ms in the P wave appearing period.

From changes in motion of the arrows in the arrow maps shown in FIGS. 14A to 14F, it is clearly seen that there exists an electric current (ring current) flowing annularly around the right and left atria of the heart. The presence of such ring current is closely related to the atrial tachycardia and the detection thereof is considered very effective in the diagnosis of atrial tachycardia.

Fifth Embodiment

Various combined images can be formed and displayed by using plural tomograms obtained by a three-dimensional XCT device and nearly parallel to the chest surface in place of the plural tomograms obtained by the MRI device in the first and second embodiments. The processing for obtaining the combined image is the same as in the first and second embodiments, including a processing of making the pixel size of a functional image obtained by the biomagnetic field measuring apparatus coincident with the pixel size of a tomogram obtained by a three-dimensional XCT device, which functional image represents functional information on the heart activity, such as an isomagnetic field map, an arrow map, an isointegral map, and an estimated position of an activated position (current source), and a processing of making a central position of a reference point in the functional image obtained by the biomagnetic field measuring apparatus coincident with a reference point (a central point of an X-ray marker image), which central position corresponds to the position of a measuring plane through which the z axis of the coordinate system (x, y, z) of the biomagnetic field measuring apparatus passes.

Sixth Embodiment

Using a chest X-ray image (X-ray transmitted image) obtained by an X-ray camera, instead of the tomogram 407 obtained by the MRI device in the first embodiment, there can be formed and displayed various combined images between the chest X-ray image and a functional image obtained by the biomagnetic field measuring apparatus, which functional image represents functional information on the heart activity, such as an isomagnetic field map, arrow map, isointegral map, and an estimated position of an activated position (current source). The processing for obtaining such combined images include a processing of making the pixel size of the functional image obtained by the biomagnetic field measuring apparatus coincident with the pixel size of the chest X-ray image, a processing of making a central position of a reference point (first reference point) in the functional image obtained by the biomagnetic field measuring apparatus coincident with the first reference point (a central point of an X-ray marker image) photographed in the chest X-ray image, which central position corresponds to the position of a measuring plane through which the z axis of the coordinate system (x, y, z) of the biomagnetic field measuring apparatus passes, and a processing of making the body axis direction of the subject to be inspected in the chest X-ray image coincident with the pixel arrangement direction in the body axis direction (the direction of connecting the first and second reference points) of the subject to be inspected in the functional image.

Since it is possible to prepare a combined image formed of an image obtained by rotating the chest X-ray image around the first reference point (a central point of an X-ray marker image) with the functional image, it is possible to form a more accurate combined image of the functional image and the morphological image. For example, by rotating the morphological image around the first reference point (a central point of an X-ray marker image) so that a center line of the backbone in the chest X-ray image and the pixel arrangement direction in the body axis direction of the subject to be inspected in the functional image become coincident with each other, there can be formed a more accurate combined image of the functional image and the morphological image.

In the measurement by the biomagnetic field measuring apparatus in each of the above embodiments, there is used, for example, lead (size: 5 mm×5 mm, thickness: 5 mm) or a vitamin compound (size: 5 mm×5 mm, thickness: 5 mm) as a marker to be affixed to each of the reference points 37 and 38. In photographing a tomogram or a blood flow image with an MRI device, a vitamin compound (size: 5 mm×5 mm, thickness: 5 mm) for example is affixed as an MRI marker to the reference point 37. The vitamin compound is projected on the image which is photographed by the MRI device. In photographing the chest X-ray image using an X-ray camera or a tomogram by a three-dimensional X-ray computed tomography (XCT) device, lead (size: 5 mm×5 mm, thickness: 5 mm), for example is affixed as an X-ray marker to the reference point 37. The lead is projected on the chest X-ray image or X-ray CT tomogram. In the chest X-ray image, if it is difficult to identify the processus xiphoideus, the position of the processus xiphoideus can be calculated by measuring the distance between the incisura jugularis and the processus-xiphoideus of the subject to be inspected with use of, for example, a ruler, then correcting the measured distance in consideration of the influence of the chest X-ray image photographing magnification to obtain a corrected distance, and assuming that the processus xiphoideus is present at a position spaced from the incisura jugularis by the corrected distance along the central axis of the subject to be inspected on the chest X-ray image.

In each of the embodiments described above, loading of data on the tomogram and blood flow image both obtained by an MRI device, data on chest X-ray image obtained by an X-ray camera, and data on tomogram obtained by a three-dimensional XCT device into the memory of the biomagnetic field measuring apparatus is performed in the following manner.

In the case where the biomagnetic field measuring apparatus, MRI device, three-dimensional XCT device, and a reader, which digitizes the light and shade of a chest X-ray image film and reads the digitized data, as image data constitute a PACS (Picture Archiving and Communications Systems), the image data is loaded online from each device into the memory of the biomagnetic field measuring apparatus.

When images formed by an MRI device, three-dimensional XCT device, and X-ray camera are obtained in film, there is used an image reader which digitizes the light and shade of the film and reads the digitized data as image data. The digitized image data is stored in a portable medium, and the image data is loaded through the portable medium into the memory of the biomagnetic field measuring apparatus. Alternatively, there may be adopted a configuration wherein an image reader and the biomagnetic field measuring apparatus are connected online with each other, and output data (digitized image data) of the image reader is loaded directly into the memory of the biomagnetic field measuring apparatus.

Figure 15:
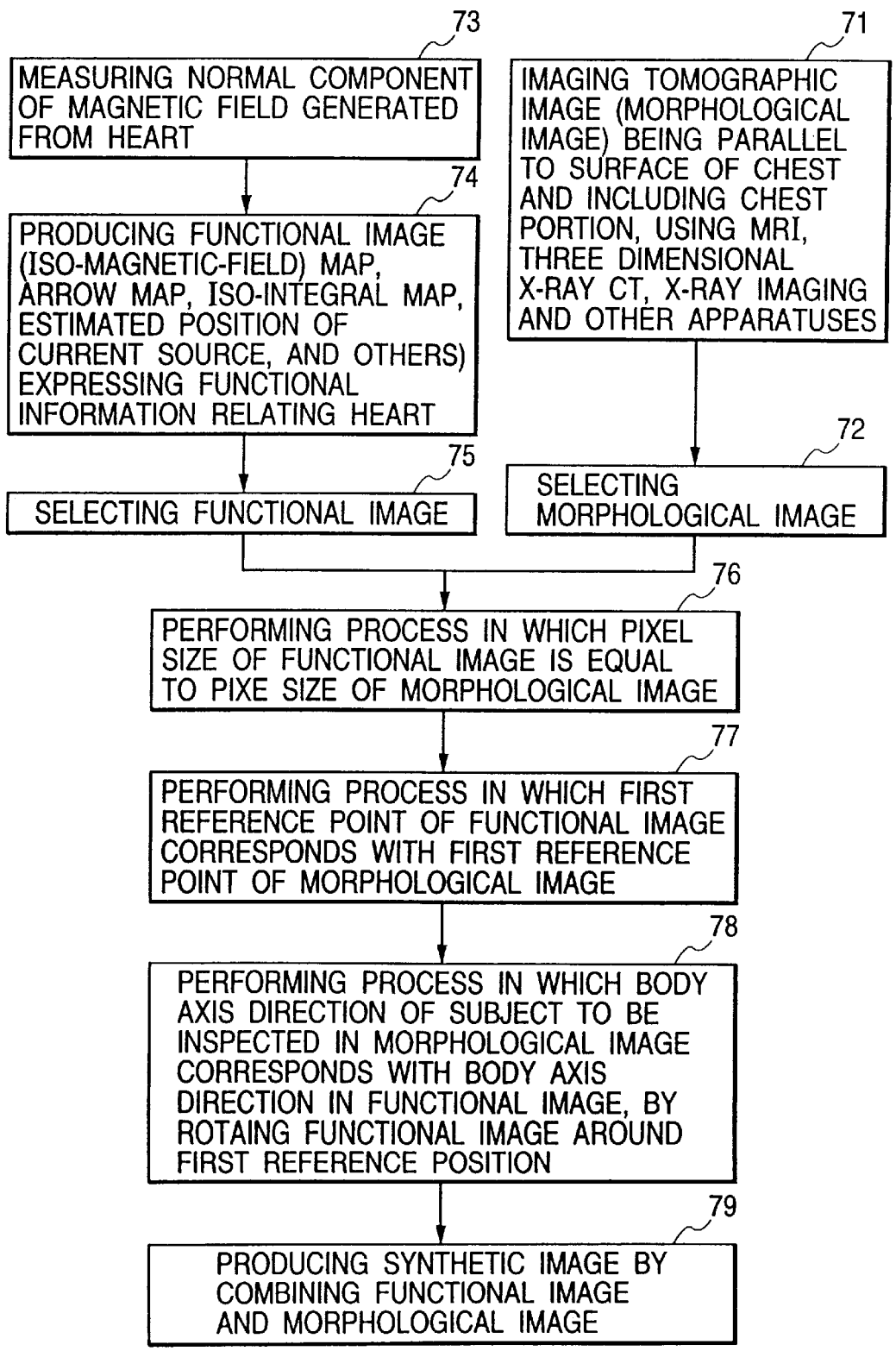
FIG. 15 is a flow diagram which shows schematically an example of the procedure used when a combined image of a biofunctional image and a morphological image is to be formed in each of the embodiments of the present invention.
Figure 16:
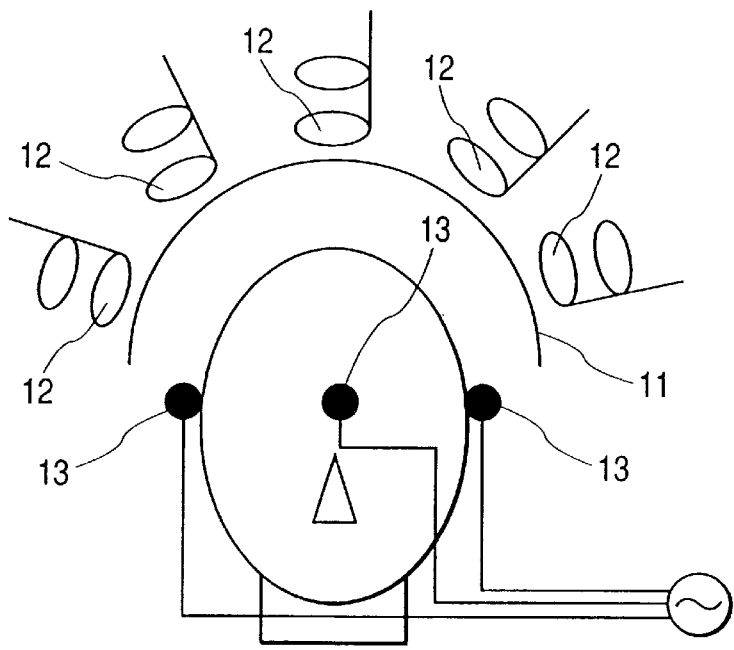
FIG. 16 is a diagram which illustrates a prior art example of specifying position coordinates of a head portion in biomagnetic field measurement for the measurement of a brain magnetic field.
Figure 17:
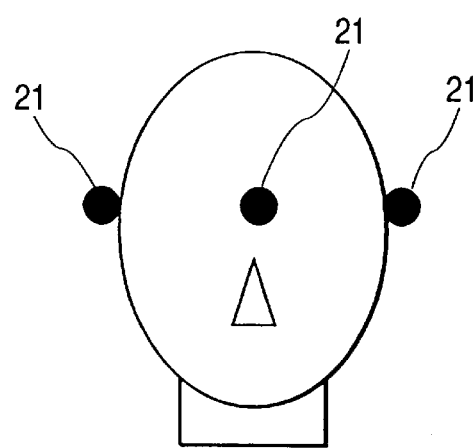
FIG. 17 is a diagram which illustrates a prior art example of specifying, with use of MRI image, markers' position coordinates for combining the results of brain magnetic field measurement with MRI image of the head portion.

FIG. 15 is a schematic diagram showing an example of a procedure for forming a combined image of the biofunctional image and the morphological image in each of the above embodiments. The procedure will be outlined below with reference to FIG. 15.

Step 1 (reference numeral 71): A morphological image included the chest is photographed by an MRI device, a three-dimensional XCT device, or an X-ray camera. With an MRI device or a three-dimensional XCT device, there are photographed a plurality of tomograms parallel to the chest surface of the subject to be inspected. With an X-ray camera, a chest X-ray image (X-ray transmitted image) is photographed from the front. In the photographing of the morphological image with any of these devices, a first marker indicative of the first reference point is disposed on the body surface of the processus xiphoideus of the subject to be inspected.

Step 2 (reference numeral 72): The morphological image obtained in step 1 (reference numeral 71) is selected.

Step 3 (reference numeral 73): First and second markers representing first and second reference points, respectively, are affixed to the body surfaces of the processus xiphoideus and the incisura jugularis, respectively, of the subject to be inspected, and a magnetic field component in the normal line direction of a magnetic field generated from the heart is measured.

Step 4 (reference numeral 74): A tangential magnetic field component of the magnetic field generated from the heart is estimated from the normal magnetic field component thus measured and, using the tangential magnetic field component, there is formed a functional image (e.g., iso-magnetic field map, arrow map, isointegral map, or an estimated current source position) which represents functional information on the activity of the heart.

Step 5 (reference numeral 75) The functional image formed in step 4 (reference numeral 74) is selected.

Step 6 (reference numeral 76): A processing is performed for making the pixel size of the functional image coincident with the pixel size of the morphological image.

Step 7 (reference numeral 77): A processing is performed for making the first reference point of the functional image coincident with that of the morphological image.

Step 8 (reference numeral 78): When the body axis direction of the subject to be inspected in the morphological image and the pixel arrangement direction in the body axis direction of the subject to be inspected in the functional image are not coincident with each other, there is performed a processing of rotating the morphological image around the first reference point to make both directions coincident with each other.

Step 9 (reference numeral 79): The functional image and the morphological image are combined into a single combined image.

It is optional which of step 1 (reference numeral 71) and step 3 (reference numeral 73) is to be executed first. There may be adopted a method involving selecting in step 5 (reference numeral 75) a plurality of functional images formed in step 4 (reference numeral 74), then forming combined images of the thus-selected plural functional images with the morphological image through the steps 6 (reference numeral 76) to 9 (reference numeral 79) and displaying them. Further, there may be adopted a method involving forming combined images of the plural functional images with plural tomograms selected from those parallel to the chest plane of the subject to be inspected and which were photographed in step 1 (reference numeral 71), and displaying them. Execution of step 8 (reference numeral 78) may be omitted.

In the present invention, as described above, there are performed (1) a processing of making the pixel size of the functional image coincident with the pixel size of the morphological image, the functional image representing a functional information on the activity of the heart such as an isomagnetic field map, an arrow map, an isointegral map, or an estimated position of an activated site (current source), which is obtained by the biomagnetic field measuring apparatus in a short time without requiring any complicated calculation, the morphological image being obtained by an MRI device, a three-dimensional XCT device, or an X-ray camera and representing the shape of the heart; and (2) a processing of making a central position of the first reference point in the functional image coincident with the first reference point (a central point of an MRI marker image or of an X-ray marker image) photographed in the morphological image, which central position of the first reference point corresponds to the position of the measuring plane through which the z axis of the coordinate system (x, y, a) in the biomagnetic field measuring apparatus passes.

Further, there is performed a processing of rotating the morphological image around the first reference point (a central point of an MRI marker image or of an X-ray marker image) photographed in the morphological image and thereby making the body axis direction of the subject to be inspected in the morphological image coincident with the pixel arrangement direction of in the body axis direction (the direction joining the first and second reference points) of the subject to be inspected in the functional image, whereby there can be formed a more accurate combined image of both the functional image and the morphological image.

Thus, an arbitrary tomogram is selected from plural tomograms which are obtained by an MRI device or a three-dimensional XCT device and which are substantially parallel to the chest surface, and a combined image of the selected tomogram with an isomagnetic field map changing with time or an arrow map also changing with time can be displayed moment by moment.

Moreover, a combined image, obtained by combining an image which represents an activated position, a tomogram obtained by an MRI device or a three-dimensional XCT device, the tomogram being substantially parallel to the chest surface and including the activated position, and an isomagnetic field map changing with time or an isointegral map also changing with time, can be displayed moment by moment. The image which represents an activated position is indicated by an arrow, for example. The root position of the arrow represents an estimated position of a current source; the length of the arrow represents the size of the current source, and the direction of the arrow indicates the direction of vector, which represents the current source projected on (x, y) plane.

Further, a combined image of a chest X-ray image (morphological image) obtained by an X-ray camera and an isomagnetic field map changing with time or an isointegral map also changing with time can be displayed moment by moment. A combined image can also be displayed moment by moment, which combined image is obtained by combining together a chest X-ray image (X-ray transmitted image), an image which represents an activated position, and an isomagnetic field map changing with time or an isointegral map also changing with time.

Although the invention has been described in its preferred form with a certain degree of particularity, it is understood that the present disclosure of the preferred form may be changed in the details of construction and a combination and a different arrangement of parts may be resorted to without departing from the spirit and the scope of the invention as hereinafter claimed.

What is claimed is:

1. A biomagnetic field measuring apparatus comprising:
 a plurality of SQUID sensors for detecting a magnetic field component in a normal line direction generated from the heart of a subject to be inspected, the SQUID sensors being arranged in two dimensions;
 a cryostat for cooling the SQUID sensors;
 a driving circuit for driving the SQUID sensors;
 a processing unit which collects magnetic waveform signals of the magnetic field component in the normal line direction detected by the SQUID sensors and which performs an arithmetic processing for the collected signals; and
 display means for displaying the result of the arithmetic processing,
 wherein the chest of the subject to be inspected is disposed below the bottom of the cryostat so that a line joining a first reference point and a second reference point becomes coincident or parallel with one direction in which centers of the SQUID sensors are arranged, the first reference point being indicated by a first marker disposed on the body surface of processus xiphoideus of the subject to be inspected, and the second reference point being indicated by a second marker disposed on the body surface of incisura jugularis of the subject to be inspected, and the processing unit executes the following processings:
 (1) a processing of forming an image from the magnetic waveform signals which image represents a functional information on the activity of the heart of the subject to be inspected;
 (2) a processing of making the pixel size of the image representative of the functional information coincident with the pixel size of a morphological image photographed by an image pickup device and including the heart of the subject to be inspected, and forming a functional image having the same pixel size as that of the morphological image;
 (3) a processing of making the position of the first reference point in the functional image coincident with the position of the first marker in the morphological image; and
 (4) a processing of forming a combined image of the functional image and the morphological image, the combined image being displayed on the display means.

2. A biomagnetic field measuring apparatus according to claim 1, wherein the processing unit performs a processing of estimating an activated position of the heart of the subject to be inspected as a current source with use of the magnetic waveform signals of the magnetic component in the normal line direction and the resulting image including the position of the current source is used as the functional image.

3. A biomagnetic field measuring apparatus according to claim 1, wherein the processing unit performs a processing of obtaining, from the magnetic field component in the normal line direction, a tangential magnetic field component of the magnetic field generated from the heart of the subject to be inspected and forming an isomagnetic field map wherein coordinate points equal in magnetic field intensity are connected together, using magnetic waveform signals of the tangential magnetic field component, the isomagnetic field map being used as the functional image.

4. A biomagnetic field measuring apparatus according to claim 1, wherein the processing unit performs a processing of obtaining, from the magnetic component in the normal line direction, a tangential magnetic field component of the magnetic field generated from the heart of the subject to be inspected and forming an arrow map wherein an activated position of the heart of the subject to be inspected is displayed as a two-dimensional current distribution, using magnetic waveform signals of the tangential magnetic field component, the arrow map being used as the functional image.

5. A biomagnetic field measuring apparatus according to claim 1, wherein the processing unit performs a processing of obtaining, from the magnetic field component in the normal line direction, a tangential magnetic field component of the magnetic field generated from the heart of the subject to be inspected and also performs a processing of integrating the magnetic waveforms in a temporal interval including a specific period of the heart activity of the subject to be inspected to obtain integral intensities, using magnetic waveform signals of the tangential magnetic field component, and forming an isointegral map wherein coordinate points equal in integral intensity are connected together, the isointegral map being used as the functional image.

6. A biomagnetic field measuring apparatus according to claim 1, wherein the processing unit performs a processing of obtaining, from the magnetic field component in the normal line direction, a tangential magnetic field component of the magnetic generated from the heart of the subject to be inspected and also performs a processing of integrating magnetic waveforms of the tangential magnetic field component in a temporal interval including two different periods of the heart activity of the subject to be inspected, using magnetic waveform signals of the tangential magnetic field component, and forming an isointegral map wherein coordinate points equal in the value of difference between integral intensities in said temporal interval are connected together, the isointegral map being used as the functional image.

7. A biomagnetic field measuring apparatus according to claim 1, wherein the morphological image is selected from a tomogram substantially parallel or perpendicular to the chest surface of the subject to be inspected which has been photographed by an MRI device, a tomogram substantially parallel or perpendicular to the chest plane of the subject to be inspected which has been photographed by a three-dimensional XCT device, and a chest X-ray image of the subject to be inspected which has been photographed by an X-ray camera.

8. A biomagnetic field measuring apparatus according to claim 1, wherein prior to the processing (4) there is performed a processing (3') of rotating the morphological image around the first reference point to make the body axis direction of the subject to be inspected in the morphological image and the pixel arrangement direction in the body axis direction of the subject to be inspected in the functional image coincident with each other.

9. A biomagnetic field measuring apparatus comprising:

a plurality of SQUID sensors for detecting a magnetic field component in a normal line direction generated from the heart of a subject to be inspected, the SQUID sensors being arranged in two dimensions;

a cryostat for cooling the SQUID sensors;

a driving circuit for driving the SQUID sensors;

a processing unit which collects magnetic waveform signals of the magnetic field component in the normal line direction detected by the SQUID sensors and which performs an arithmetic processing for the collected signals; and display means for displaying the result of the arithmetic processing, wherein the chest of the subject to be inspected is disposed in contact with the bottom of the cryostat so that a line joining a first reference point and a second reference point extends in one direction in which centers of the SQUID sensors are arranged, the first reference point being indicated by a first marker disposed on the body surface of a first point of the chest of the subject to be inspected, and the second reference point being indicated by a second marker disposed on the body surface of a second point of the chest of the subject to be inspected, and the processing unit executes the following processings:

(1) a processing of forming an image from the magnetic waveform signals which image represents a functional information on the activity of the heart of the subject to be inspected;

(2) a processing of making the pixel size of the image representative of the functional information coincident with the pixel size of a morphological image of the chest of the subject to be inspected which has been photographed by an image pickup device and forming a functional image having the same pixel size as that of the morphological image;

(3) a processing of making the position of the first reference point in the functional image coincident with the position of the first marker in the morphological image, and (4) a processing of forming a combined image of the functional image and the morphological image, the combined image being displayed on the display means.

10. A biomagnetic field measuring apparatus according to claim 9, wherein the first point is processus xiphoideus of the subject to be inspected and the second point is incisura jugularis.

11. A biomagnetic field measuring apparatus according to claim 9, further including, prior to the processing (4), a processing (3') of rotating the morphological image around the first reference point to make the body axis direction of the subject to be inspected in the morphological image and the pixel arrangement direction in the body axis direction of the subject to be inspected in the functional image coincident with each other.

12. A biomagnetic field measuring apparatus comprising:

a bed;

a support for supporting the bed;

a plurality of SQUID sensors arranged in x and y directions;

a cryostat for cooling the plural SQUID sensors, the cryostat having on an outer peripheral surface of the bottom thereof an xz marking which represents an xz plane of a coordinate system (x, y, z) and a yz marking which represents a yz plane of the coordinate system;

a gantry fixed to a floor surface to support the cryostat;

a first laser source which is fixed to a frame fixed to the gantry and which generates a first sectorial laser beam spreading sectorially in the xz plane;

a second laser source which is fixed to a frame fixed to the bed support and which generates a second sectorial laser spreading sectorially in the yz plane;

a third laser source which is fixed to a frame fixed to the floor surface or a ceiling and which generates a dot-like laser beam, the dot-like laser beam being radiated obliquely to the surface of the bed so as to intersect the first and second sectorial laser beams;

first position changing means for changing an irradiating direction of the first sectorial laser beam so as to irradiate the xz marking;

second position changing means for changing an irradiating direction of the second sectorial laser beam so as to irradiate the yz marking;

third position changing means for changing an irradiating direction of the dot-like laser beam so as to irradiate an intersecting line of the first and second sectorial laser beams and also irradiate an intersecting point of the z axis and the bed surface;

x direction moving means for moving the bed support in x direction on the floor surface;

y direction moving means for moving the bed in y direction on the bed support;

z direction moving means for moving the bed in z direction on the bed support; and distance measuring means for measuring the distance between the bed and the floor surface.

13. A biomagnetic field measuring apparatus comprising:

a plurality of SQUID sensors for detecting a magnetic field generated from the heat of a subject to be inspected laid on a bed, the plural SQUID sensors being arranged in x and y directions;

a cryostat for cooling the plural SQUID sensors, the cryostat having on an outer peripheral surface of the bottom thereof an xz marking which represents an xz plane of a coordinate system (x, y, z) and a yz marking which represents a yz plane of the coordinate system;

a first laser source for generating a first sectorial laser beam which is spread sectorially in the xz plane;

a second laser source for generating a second sectorial laser beam which is spread sectorially in the yz plane;

a third laser source for generating a dot-like laser beam, the dot-like laser beam being radiated to the surface of the bed obliquely so as to intersect the first and second sectorial laser beams;

first position changing means for changing an irradiating direction of the first sectorial laser beam so as to irradiate the xz marking;

second position changing means for changing an irradiating direction of the second sectorial laser beam so as to irradiate the yz marking;

third position changing means for changing an irradiating direction of the dot-like laser beam so as to irradiate an intersecting line of the first and second sectorial laser beams and also irradiate an intersecting point of the z axis and the bed surface;

x direction moving means for moving the bed in x direction so that in the xz plane the second sectorial laser passes through a first reference point indicated by a first marker disposed on the body surface of processus xiphoideus of the subject to be inspected and also passes through a second reference point indicated by a second marker disposed on the body surface of incisura jugularis of the subject to be inspected;

y direction moving means for moving the bed in y direction so that the first sectorial laser beam passes through the first reference point;

distance measuring means for measuring the distance between the bed and a floor surface on which the bed is placed; and z direction moving means which moves the bed in z direction until an irradiation point of the dot-like laser beam becomes coincident with the first reference point and which, after subsequent measurement of the distance between the bed and the floor surface by the distance measuring means, moves the bed in z direction until the body surface of the subject to be inspected comes into contact with the bottom of the cryostat, wherein the chest of the subject to be inspected is disposed below the bottom of the cryostat so that a line joining the first and second reference points becomes coincident or parallel with one direction in which centers of the SQUID sensors are arranged.

14. A method for positioning a subject to be inspected for a biomagnetic field measuring apparatus, the biomagnetic filed measuring apparatus comprising:

a bed;

a plurality of SQUID sensors arranged in x and y directions; and a cryostat for cooling the plural SQUID sensors, the cryostat having on an outer peripheral surface of the bottom thereof an xz marking which represents an xz plane of a coordinate system (x, y, z) and a yz marking which represents a yz plane of the coordinate system, the method for positioning the subject to be inspected comprising the steps of:

(1) setting an irradiating direction of a first sectorial laser beam so as to irradiate the xz marking, the first sectorial laser beam spreading sectorially in the xz plane;

(2) setting an irradiating direction of a second sectorial laser beam so as to irradiate the yz marking, the second sectorial laser beam spreading in the yz plane;

(3) setting an irradiating direction of a dot-like laser beam, which is radiated to the surface of the bed obliquely so as to intersect the first and second sectorial laser beams, in such a manner that the dot-like laser beam irradiates an intersecting line of the first and second laser beams and also irradiates an intersecting point of z axis and the bed surface;

(4) setting an irradiating direction of the second sectorial laser beam so that in the yz plane the second sectorial laser beams passes through a first reference point indicated by a first marker disposed on the body surface of a first point of the chest of the subject to be inspected and also passes through a second reference point indicated by a second marker disposed on the body surface of a second point of the chest of the subject to be inspected;

(5) moving the bed in x direction so that the second sectorial laser beam irradiates the yz marking; and (6) moving the bed in y direction so that the first sectorial laser beam passes through the first reference point, wherein the chest of the subject to be inspected is disposed below the bottom of the cryostat so that a line joining the first and second reference points becomes coincident or parallel with one direction in which centers of the SQUID sensors are arranged.

15. A positioning method according to claim 14, further including the steps of:

(7) moving the bed in z direction until an irradiation point of the dot-like laser beam becomes coincident with the first reference point; and (8) moving the bed in z direction until the body surface of the subject to be inspected comes into contact with the bottom of the cryostat and determining the distance between the first reference point and the bottom of the cryostat.

16. A positioning method according to claim 14, wherein the first point is processus xiphoideus of the subject to be inspected and the second point is incisura jugularis of the subject to be inspected.

17. A method for positioning a subject to be inspected for a biomagnetic field measuring apparatus, the biomagnetic field measuring apparatus comprising:

a bed;

a support for supporting the bed;

a plurality of SQUID sensors arranged in x and y directions;

a cryostat for cooling the plural SQUID sensors, the cryostat having on an outer peripheral surface of the bottom thereof an xz marking which represents an xz plane of a coordinate system (x, y, z) and a yz marking which represents a yz plane of the coordinate system;

a gantry fixed to a floor surface to support the cryostat;

a first laser source which is fixed to a frame fixed to the gantry and which generates a first sectorial laser beam spreading sectorially in the xz plane;

a second laser source which is fixed to a frame fixed to the bed support and which generates a second sectorial laser beam spreading in the yz plane; and a third laser source which is fixed to a frame fixed to the floor surface or a ceiling and which generates a dot-like laser beam, the dot-like laser being radiated obliquely to the surface of the bed so as to intersect the first and second sectorial laser beams, the method for positioning the subject to be inspected comprising the steps of:
(1) setting an irradiating direction of the first sectorial laser beam so as to irradiate the xz marking;
(2) setting an irradiating direction of the second sectorial laser beam so as to irradiate the yz marking;
(3) setting an irradiating direction of the dot-like laser beam so as to irradiate an intersecting line of the first and second sectorial laser beams and also irradiate an intersecting point of z axis and the bed surface;
(4) setting an irradiating direction of the second sectorial laser beam so that in the yz plane the second sectorial laser beam passes through a first reference point indicated by a first marker disposed on the body surface of a first point of the chest of the subject to be inspected and also passes through a second reference point indicated by a second marker disposed on the body surface of a second point of the chest of the subject to be inspected;
(5) moving the bed in x direction so that the second sectorial laser beam irradiates the yz marking; and
(6) moving the bed in y direction so that the first sectorial laser beam passes through the first reference point, wherein the chest of the subject to be inspected is disposed below the bottom of the cryostat so that a line joining the first and second reference points becomes coincident or parallel with one direction in which centers of the SQUID sensors are arranged.

18. A positioning method according to claim 17, further including the steps of:
(7) moving the bed in z direction until an irradiation point of the dot-like laser beam becomes coincident with the first reference point; and
(8) moving the bed in z direction until the body surface of the subject to be inspected comes into contact with the bottom of the cryostat and determining the distance between the first reference point and the bottom of the cryostat.

19. A positioning method according to claim 17, wherein the first point is processus xiphoideus of the subject to be inspected and the second point is incisura jugularis of the subject to be inspected.

* * * * *